United States Patent
Saito et al.

(10) Patent No.: US 8,216,833 B2
(45) Date of Patent: Jul. 10, 2012

(54) COSMID VECTOR

(75) Inventors: Izumu Saito, Tokyo (JP); Yumi Saito, Tokyo (JP)

(73) Assignees: Izumu Saito, Tokyo (JP); Dainippon Sumitomo Pharma Co., Ltd., Osaka (JP)

(*) Notice: Subject to any disclaimer, the term of this patent is extended or adjusted under 35 U.S.C. 154(b) by 1381 days.

(21) Appl. No.: 10/553,639

(22) PCT Filed: Nov. 19, 2003

(86) PCT No.: PCT/JP03/14760
§ 371 (c)(1),
(2), (4) Date: Mar. 9, 2006

(87) PCT Pub. No.: WO2004/094643
PCT Pub. Date: Nov. 4, 2004

(65) Prior Publication Data
US 2006/0172421 A1 Aug. 3, 2006

(30) Foreign Application Priority Data
Apr. 18, 2003 (JP) ................................ 2003-113578

(51) Int. Cl.
*C12N 15/861* (2006.01)
*C12N 15/70* (2006.01)

(52) U.S. Cl. .................................................. 435/320.1

(58) Field of Classification Search ........................ None
See application file for complete search history.

(56) References Cited

U.S. PATENT DOCUMENTS

| | | | |
|---|---|---|---|
| 5,700,470 | A | 12/1997 | Saito et al. |
| 6,740,515 | B1 | 5/2004 | Saito et al. |
| 2002/0005845 | A1 | 1/2002 | Kondo et al. |
| 2002/0058045 | A1 | 5/2002 | Mizuguchi et al. |

FOREIGN PATENT DOCUMENTS

| | | |
|---|---|---|
| EP | 1201761 A1 | 2/2002 |
| JP | 11-332560 A | 12/1999 |
| JP | 2000152781 | 6/2000 |
| JP | 2002272480 | 9/2002 |
| WO | WO 01/59071 A2 | 8/2001 |

OTHER PUBLICATIONS

Danthinne, X. et al., "New tools for the generation of E1- and/or E3-substituted adenoviral vectors", 2000, Gene Ther., vol. 7: pp. 80-87.*

Hiroyuki Mizuguchi et al., A Simple Method for Constructing E1- and E1/E4-Deleted Recombinant Adenoviral Vectors, Human Gene Therapy, vol. 10, Aug. 10, 1999, pp. 2013-2017, Mary Ann Liebert, Inc.

Kathleen L. Berkner et al., Generation of Adenovirus by Transfection of Plasmids, Nucleic Acids Research, vol. 11, No. 17, 1983, pp. 6003-6020, IRL Press Limited, Oxford, England.

Sanae Miyake et al., Efficient Generation of Recombinant Adenoviruses Using Adenovirus DNA-terminal Protein Complex and a Cosmid Bearing the Full-length Virus Genome, Proc. Natl. Acad. Sci. USA, vol. 93, Feb. 1996, pp. 1320-1324, Medical Sciences.

Andrew J. Bett et al., An Efficient and Flexible System for Construction of Adenovirus Vectors with Insertions or Deletions in Early Regions 1 and 3, Proc. Natl. Acad. Sci. USA, vol. 91, Sep. 1994, pp. 8802-8806, Medical Sciences.

Hiroyuki Mizuguchi et al., Efficient Construction of a Recombinant Adenovirus Vector by an Improved in Vitro Ligation Method, Human Gene Therapy, vol. 9, Nov. 20, 1998, pp. 2577-2583, Mary Ann Liebert, Inc.

The 25th Annual Meeting of the Molecular Biology Society of Japan, Program and Abstracts, Pacifico Yokohama, Dec. 11-14, 2002, Yokohama, Japan (6 pages).

H. Kojima et al., "Generation of Recombinant Adenovirus Vector with Infectious Adenoviral Genome Released from Cosmid-Based Vector by Simple Procedure Allowing Complex Manipulation", *Biochem. Biophys. Res. Commun.*, vol. 246, 1998, pp. 868-872.

X. Danthinne et al., "New vectors for the construction of double recombinant adenovirus", *J. Virol. Methods*, vol. 81, 1999, pp. 11-20.

Office Action mailed Sep. 1, 2009, for JPA 2004-571103.
Office Action mailed Dec. 1, 2009, for JPA 2004-571103.
Kondo et al., "Gene Engineering of the Adenovirus Vector", *Virus*, 57:37-46 (2007).

* cited by examiner

*Primary Examiner* — Michael Burkhart
(74) *Attorney, Agent, or Firm* — Sughrue Mion, PLLC

(57) ABSTRACT

A novel cosmid vector and the like effectively used in generating a recombinant adenoviral vector are provided. More specifically, there are provided a cosmid vector characterized by:
(1) containing an adenoviral genome having adenoviral inverted terminal repeat sequences each having a complete nucleotide sequence,
(2) having a deletion in an adenovirus E1 gene region, and
(3) containing a restriction enzyme recognition sequence not present in the adenoviral genome, on both sides of the adenoviral genome;
a method of generating a recombinant adenoviral vector using the cosmid vector; and a reagent for generating a recombinant adenoviral vector containing the cosmid vector as a component.

11 Claims, 9 Drawing Sheets

COSMID VECTOR

TECHNICAL FIELD

The present invention relates to a novel cosmid vector, and more particularly to a novel cosmid vector effectively used in preparing a recombinant adenoviral vector.

BACKGROUND ART

A recombinant adenoviral vector begun to be widely used because it has been recognized as a useful tool not only in gene therapy but also in the basic research field such as analysis of a gene-function. Following three methods are known as a method for generating a first-generation adenoviral vector: a method of Graham et al. (Bett, A. J. et al., Proc. Natl. Acad. Sci. USA, 91: 8802-8806 (1994)) is that, first the full-length adenovirus genome was divided into two parts and cloned into plasmids respectively, then a recombinant adenovirus vector is obtained by homologous recombination between a plasmid in which an expression unit of a desired gene was inserted in the E1-gene deletion site and the other plasmid whose adenovirus genome sequence is partially overlapped with the first plasmid;

a cloned-genome introducing method which become commercially available recently, in which an expression unit of a desired gene is inserted into a cloned full-length viral genome; (JP-A-11-332560, Berkner, K. L. et al., Nuc. Acids Res., 11: 6003-6020 (1983); Mizuguchi, H. et al., Hum. Gene Ther., 10: 2013-2017 (1999); and H. Mizuguchi et al., Experimental medicine, 20: 1799-1804 (2002));

A COS-TPC method using a viral genome with a terminal protein, developed by the present inventors (JP-A-8-308585 and Miyake S. et al., Proc. Natl. Acad. Sci. USA, 93: 1320-1324 (1996)).

The principle of the cloned-genome introducing method has been known from about 20 years ago. Despite of a simple method, a generation efficiency of adenoviruses of this method is low, so that this generation method is not considered practical. The COS-TPC method developed by the present inventors is based on the principle of homologous recombination between a cosmid vector in which a full-length adenoviral genome is cloned and an adenoviral genome DNA with a terminal protein (DNA-TPC) digested with a restriction enzyme such as EcoT22I. Desired recombinant adenoviruses can be efficiently obtained by the COS-TPC method. Thus, numerous example are reported which show generation of an adenovirus vector expressing a desired gene having a potential effect on cells. As is evident from this, the COS-TPC method has been considered variable. However, the COS-TPC method is intricate, so that the COS-TPC method is not always required even for the case where it is satisfactory if a desired recombinant adenoviral vector can be generated even though the generation efficiency is slightly low. From this point of view, a simple "cloned-genome introducing method" has been reconsidered. However, a cosmid vector conventionally used in the COS-TPC method has a deletion at both ends of the adenoviral genome. Therefore, even if the cells are transformed with the cosmid vector in which the viral genome portion is cleaved out and linearized, it is impossible to generate the virus. To overcome this, in order to applicate widely this generation method, it has been desired to develop a simple and practical method for constructing a cosmid vector applicable to not only the COS-TPC method but also the cloned full-length genome introducing method (see FIG. 1).

DISCLOSURE OF THE INVENTION

An object of the present invention is to provide a novel cosmid vector efficiently used in generating a recombinant adenoviral vector. More specifically, the object of the present invention is to provide a simple and practical cosmid vector applicable to both a COS-TPC method and a cloned full-length genome introducing method.

Another object of the present invention is to provide a cosmid vector or a plasmid vector capable of more efficiently generating a recombinant adenoviral vector by introducing a multiple kinds of restriction enzyme recognition sequences not being present in the adenoviral genome, into both sides of the adenoviral genome.

The present inventors have conducted intensive studies with the view to attain the aforementioned objects. As a result, they developed a novel cosmid vector by repairing the deletion parts at both ends of the adenoviral genome to the full-length in the cosmid vector used in the COS-TPC method, and further introducing a restriction site (for example, TTCGAA) not existing in the adenoviral genome, into outside the repaired deletion parts. They demonstrated that the novel cosmid vector has various advantages over a conventional cosmid vector and can be extremely efficiently used for generating a recombinant adenoviral vector. Furthermore, they first found that it is possible to introduce a restriction site not only one kind of site but also multiple kinds of sites.

The present invention has achieved based on the aforementioned findings.

More specifically, the present invention relates to:

1) A cosmid vector characterized by:
  (1) containing an adenoviral genome having adenoviral inverted terminal repeat sequences each having a complete nucleotide sequence,
  (2) having a deletion in an adenovirus E1 gene region, and
  (3) containing a restriction enzyme recognition sequence not present in the adenoviral genome, on both sides of the adenoviral genome;

2) The cosmid vector according to item 1), characterized by comprising a drug resistant gene, a replication origin, a spacer sequence and a COS region, in addition to the adenoviral genome;

3) The cosmid vector according to item 2), characterized in that the drug resistant gene and the replication origin are present between a left inverted terminal repeat sequence of the adenoviral genome and the spacer sequence;

4) The cosmid vector according to item 3), characterized in that the drug resistant gene, the replication origin, the spacer sequence and the COS region are arranged in this order from outside of the left inverted terminal repeat sequence of the adenoviral genome toward a right inverted terminal repeat sequence;

5) The cosmid vector according to any one item 1) to 4), comprising TTCGAA as a restriction enzyme recognition sequence present on both sides of the adenoviral genome;

6) The cosmid vector according to item 5), characterized in that the restriction enzyme which recognized TTCGAA is Csp45I, BspT104I or BstBI;

7) The cosmid vector according to any one of items 1) to 6), comprising a nucleotide sequence recognized by a restriction enzyme for inserting a foreign gene into an E1 gene deletion site;

8) The cosmid vector according to item 7), characterized in that the restriction enzyme is SwaI;

9) The cosmid vector according to item 7) or 8), further comprising a CAG promoter or an EF-1α promoter in the E1 gene deletion site;

10) A method of generating a recombinant adenoviral vector characterized by comprising digesting the cosmid vector according to any one of items 1) to 9) with a restriction enzyme and transforming a cell with the cosmid vector;

11) The method of generating a recombinant adenoviral vector according to item 10), characterized in that the restriction enzyme is Csp45I, BspT104I or BstBI;

12) A reagent for generating a recombinant adenoviral vector comprising the cosmid vector according to any one of items 1) to 9) as a component;

13) A cosmid vector or plasmid vector characterized by:
   (1) containing an adenoviral genome having adenoviral inverted terminal repeat sequences each having a complete nucleotide sequence,
   (2) having a deletion in an adenovirus E1 gene region, and
   (3) containing multiple kinds of restriction enzyme recognition sequences not present in the adenoviral genome, on both sides of the adenoviral genome;

14) The vector according to item 13), comprising, on both sides of the adenoviral genome, at least two kinds of restriction enzyme recognition sequences selected from
   (a) TTCGAA recognized by a restriction enzyme of Csp45I, BspT104I, or BstBI,
   (b) TTAATTAA recognized by a restriction enzyme PacI, and
   (c) ATCGAT recognized by a restriction enzyme ClaI or BspDI;

15) The vector according to item 14), comprising at least
   (a) TTCGAA recognized by a restriction enzyme Csp45I, BspT104I, or BstBI, and
   (b) TTAATTAA recognized by a restriction enzyme PacI; 16) The vector according to item 14), comprising at least
   (a) TTCGAA recognized by a restriction enzyme Csp45I, BspT104I, or BstBI, and
   (c) ATCGAT recognized by a restriction enzyme ClaI or BspDI;

17) The vector according to item 13), comprising two kinds of restriction enzyme recognition sequences not present in the adenoviral genome, on both sides of the adenoviral genome;

18) The vector according to item 17), comprising two kinds of restriction enzyme recognition sequences selected from
   (a) TTCGAA recognized by a restriction enzyme Csp45I, BspT104I, or BstBI,
   (b) TTAATTAA recognized by a restriction enzyme PacI, and
   (c) ATCGAT recognized by a restriction enzyme ClaI or BspDI;

19) The vector according to item 18), comprising
   (a) TTCGAA recognized by a restriction enzyme Csp45I, BspT104I, or BstBI, and
   (b) TTAATTAA recognized by a restriction enzyme PacI;

20) The vector according to item 18), comprising
   (a) TTCGAA recognized by a restriction enzyme Csp45I, BspT104I, or BstBI, and
   (c) ATCGAT recognized by a restriction enzyme ClaI or BspDI;

21) The vector according to item 13), comprising three kinds of restriction enzyme recognition sequences not present in the adenoviral genome, on both sides of the adenoviral genome;

22) The vector according to item 21), comprising three kinds of restriction enzyme recognition sequences of
   (a) TTCGAA recognized by a restriction enzyme Csp45I, BspT104I, or BstBI,
   (b) TTAATTAA recognized by a restriction enzyme PacI, and
   (c) ATCGAT recognized by a restriction enzyme ClaI or BspDI;

23) The vector according to any one of items 13) to 22), comprising a nucleotide sequence recognized by a restriction enzyme for inserting a foreign gene into an E1 gene deletion site;

24) The vector according to item 23), characterized in that the restriction enzyme is SwaI;

25) The vector according to item 23) or 24), further comprising a CAG promoter or an EF-1α promoter in the E1 gene deletion site;

26) The vector according to any one of items 13) to 25), characterized in that the vector is a cosmid vector;

27) The vector according to item 26), characterized by comprising a drug resistant gene, a replication origin, a spacer sequence and a COS region, in addition to the adenoviral genome;

28) The cosmid vector according to item 27), characterized in that the drug resistant gene and the replication origin are present between the left inverted terminal repeat sequence of the adenoviral genome and the spacer sequence;

29) The cosmid vector according to item 28), characterized in that the drug resistant gene, the replication origin, the spacer sequence and the COS region are arranged in this order from outside of the left inverted terminal repeat sequence of the adenoviral genome toward the right terminal inverted terminal repeat;

30) The method of generating a recombinant adenoviral vector, characterized by comprising digesting the vector according to any one of items 13) to 29) with a restriction enzyme and transforming a cell with the vector;

31) The method of generating a recombinant adenoviral vector according to item 30), characterized in that the restriction enzyme is Csp45I, BspT104I or BstBI;

32) The method of generating a recombinant adenoviral vector according to item 30), characterized in that the restriction enzyme is PacI;

33) The method of generating a recombinant adenoviral vector according to item 30), characterized in that the restriction enzyme is ClaI or BspDI; and 34) A reagent for generating a recombinant adenoviral vector, comprising the vector according to any one of items 13) to 29), as a component.

Figure 1:
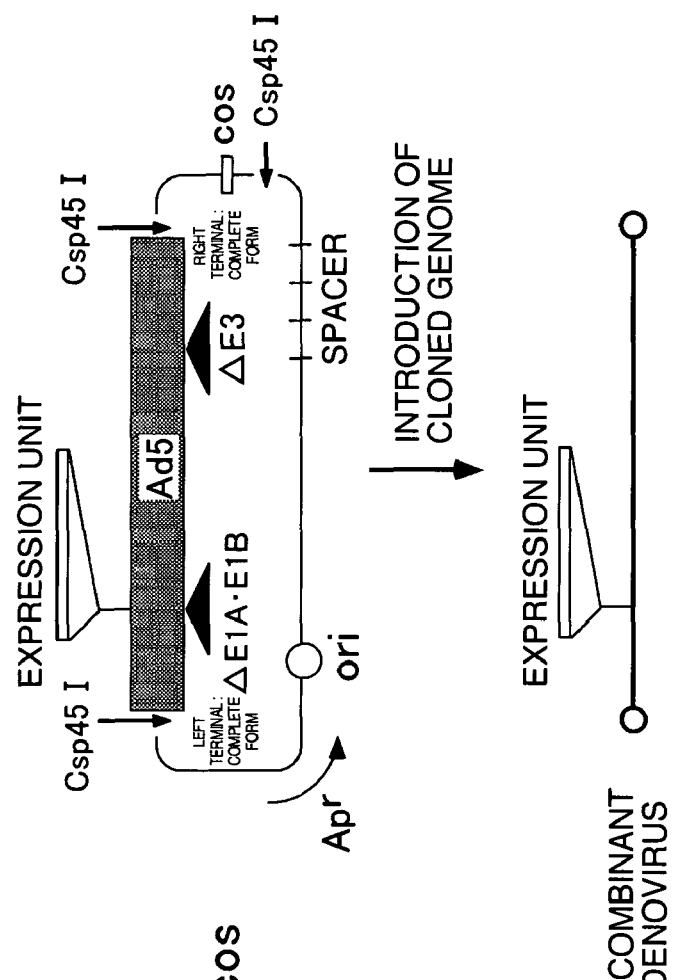
FIG. 1 is a schematic illustration of a method for generating a recombination adenovirus using a cosmid vector of the present invention. In the figure, DNA-TPC represents adenoviral genomic DNA attached with a terminal protein, Ad5 represents genome of human adenovirus Type-5; $Ap^r$ represents an ampicillin resistant gene, ori represents *Escherichia coli* replication origin, and COS represents a COS region; and thick solid arrows described in DNA-TPC each points out a recognition site of a restriction enzyme, EcoT22I.
Figure 1:
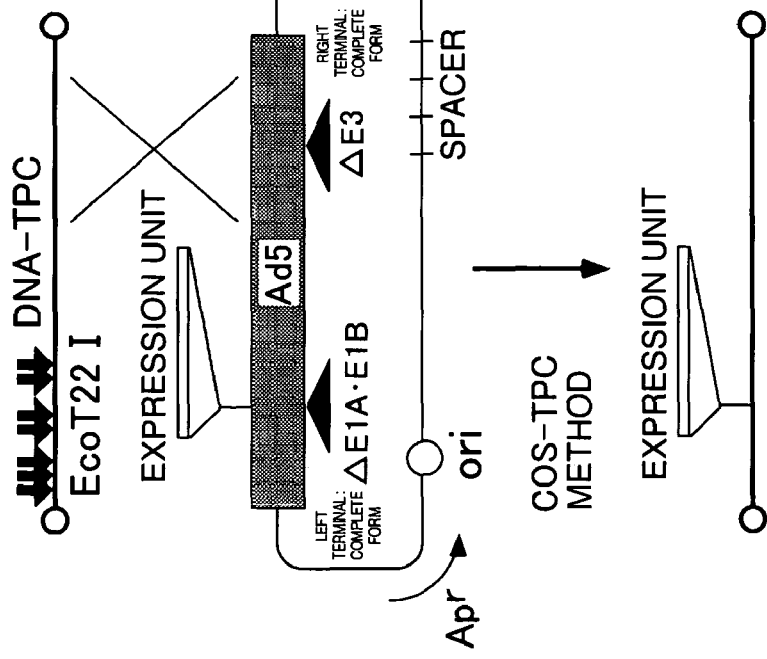

In the COS-TPC method shown in FIG. 1-A, a recombinant adenovirus is generated by transforming a cell with a cosmid vector not digested with a restriction enzyme in combination with DNA-TPC digested with the restriction enzyme.

In the "cloned-genome introducing method" shown in FIG. 1-B, a cosmid vector is digested with restriction enzyme Csp45I and then transforms a cell to generate a recombinant adenovirus.

Figure 2:
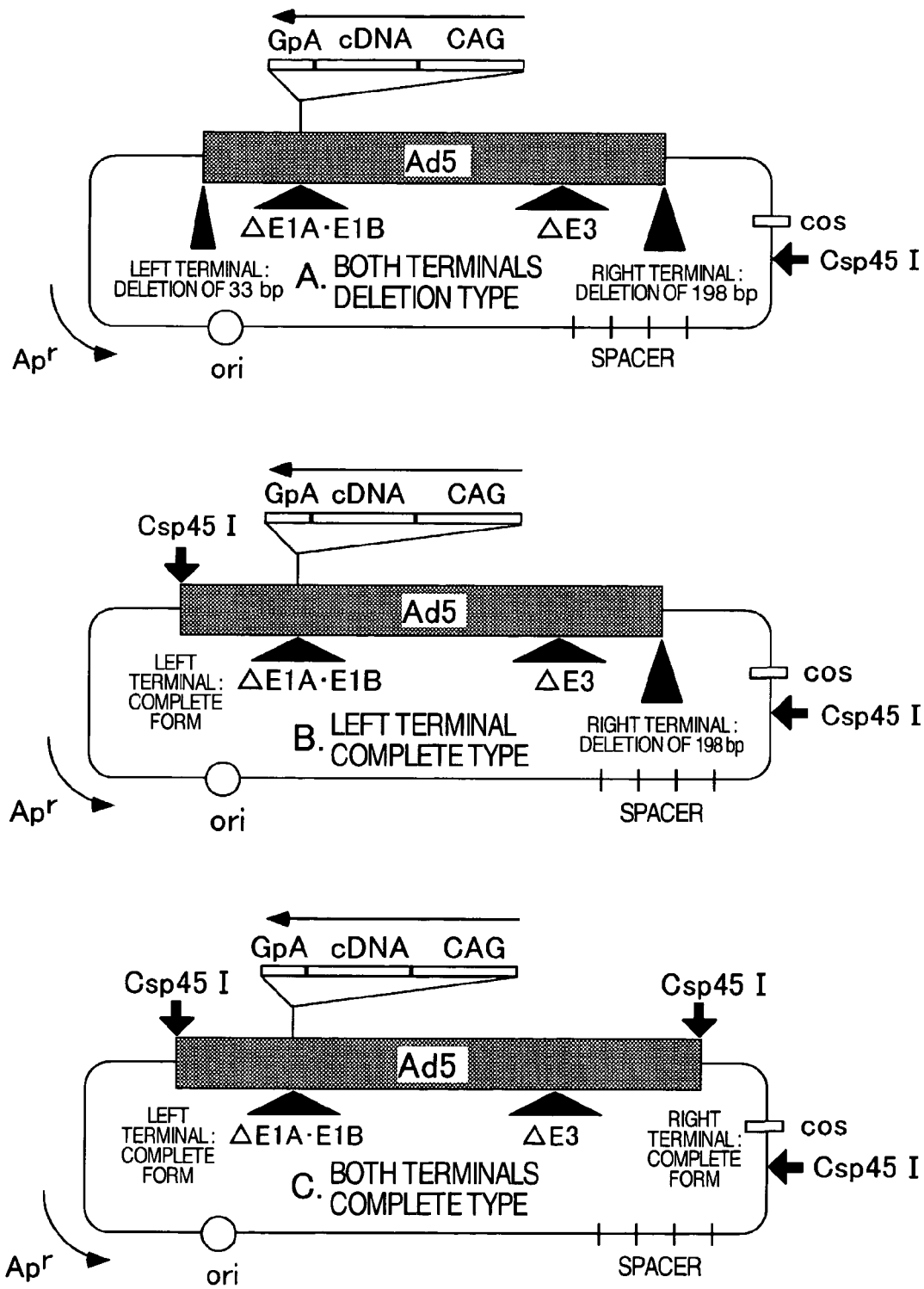

FIG. 2 is a schematic illustration of the cosmid vector used in the present invention. In the figure, CAG represents a CAG promoter and GpA represents β-globin polyadenylation signal.

Figure 3:
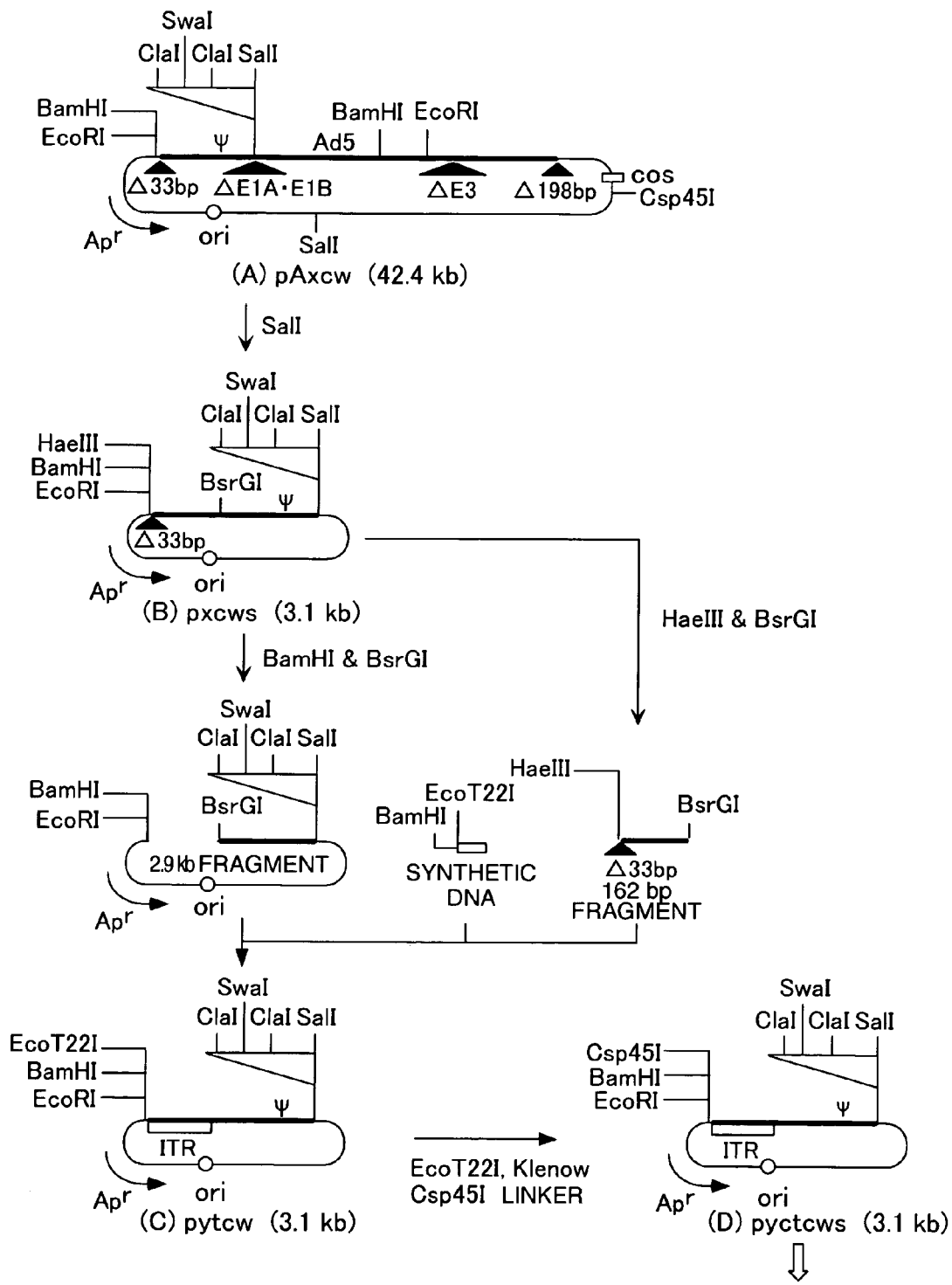

FIG. 3 is a schematic illustration showing a method of constructing a cosmid vector of the present invention. In the figure, a symbol ψ represents an adenovirus packaging signal, and ITR represents the sequence of an inverted terminal repeat.

Figure 4:
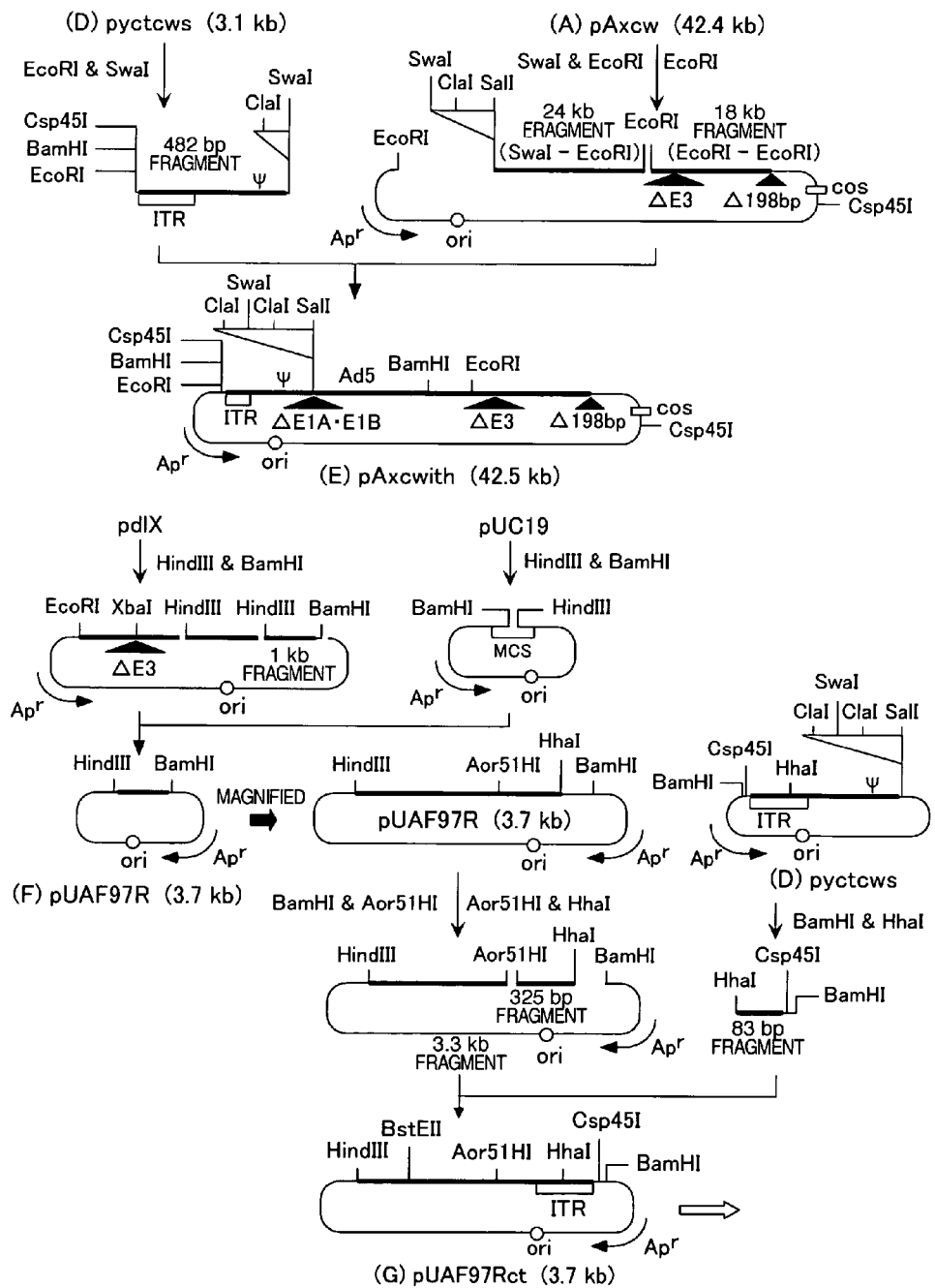
Figure 5:
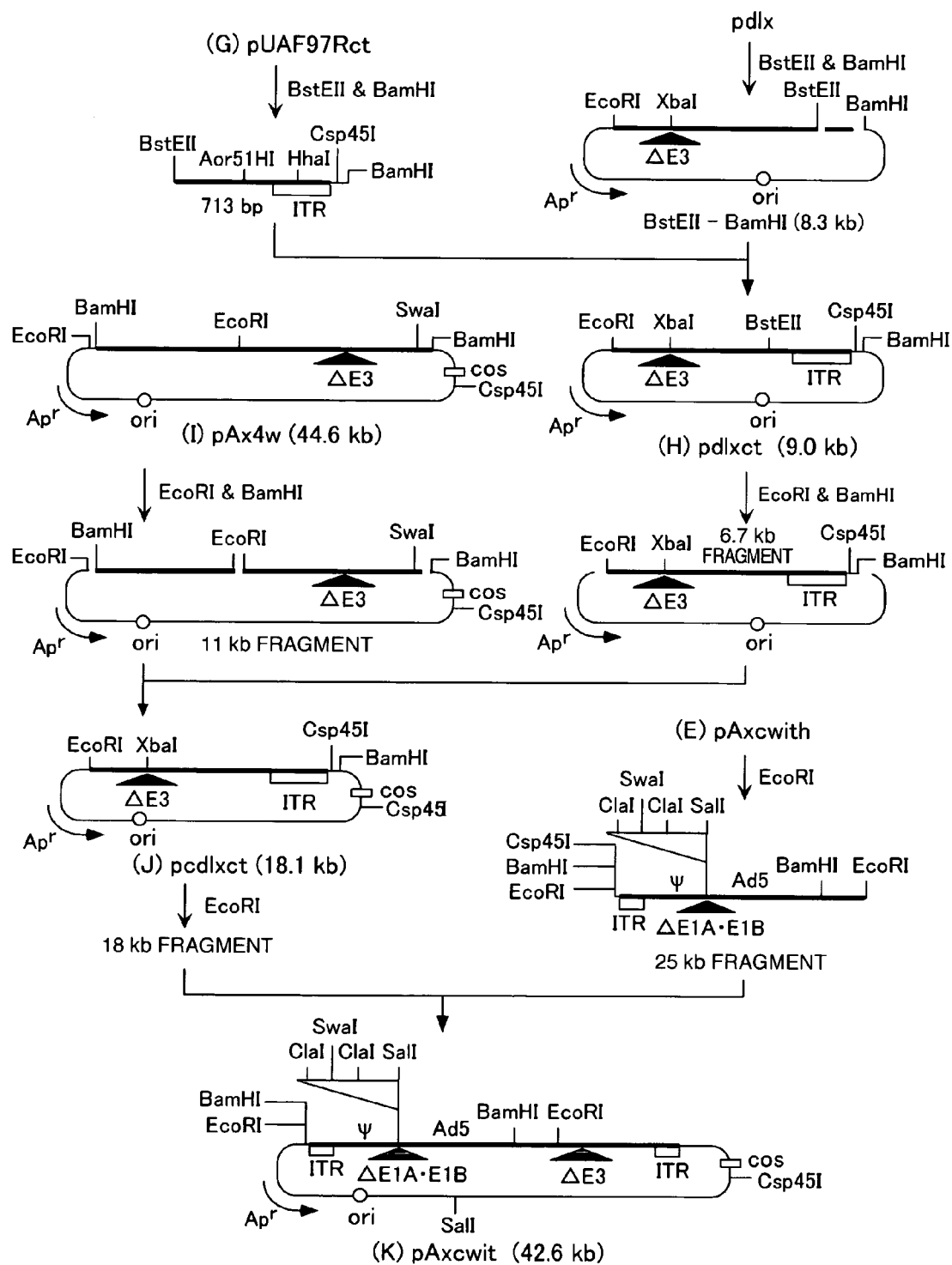

Note that identification symbols (A) to (K) in front of plasmid names or cosmid names are commonly used in FIGS. 3 to 5.

FIG. 4 is a schematic illustration (continued from FIG. 3) showing a method of constructing a cosmid vector of the present invention.

FIG. 5 is a schematic illustration (continued from FIG. 4) showing a method of constructing a cosmid vector of the present invention.

Figure 6:
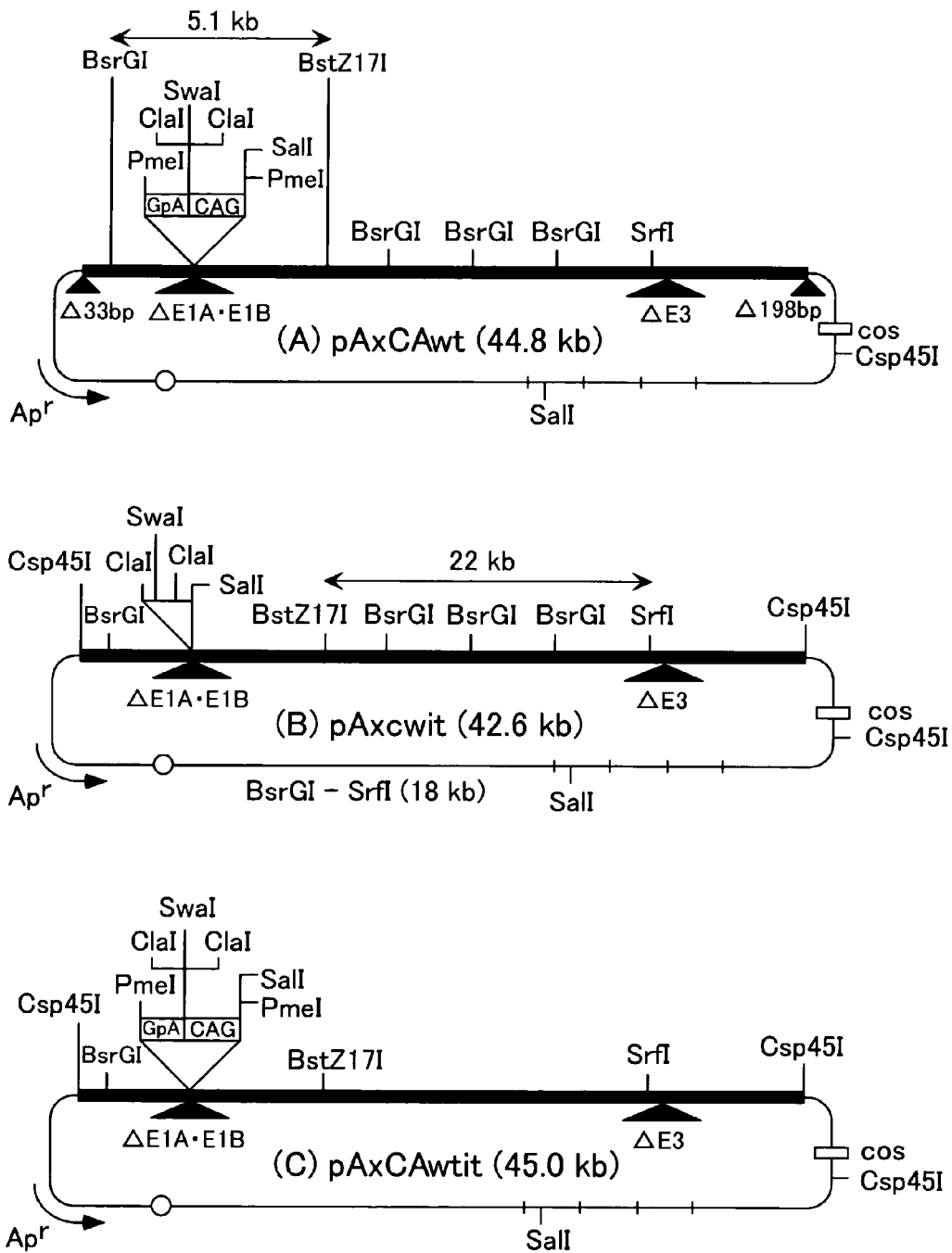

FIG. 6 is a schematic illustration showing the structures of a cosmid vector pAxCAwt (both terminals deletion type), pAxcwit (both terminals complete type), and pAxCAwtit (both terminals complete type).

Figure 7:
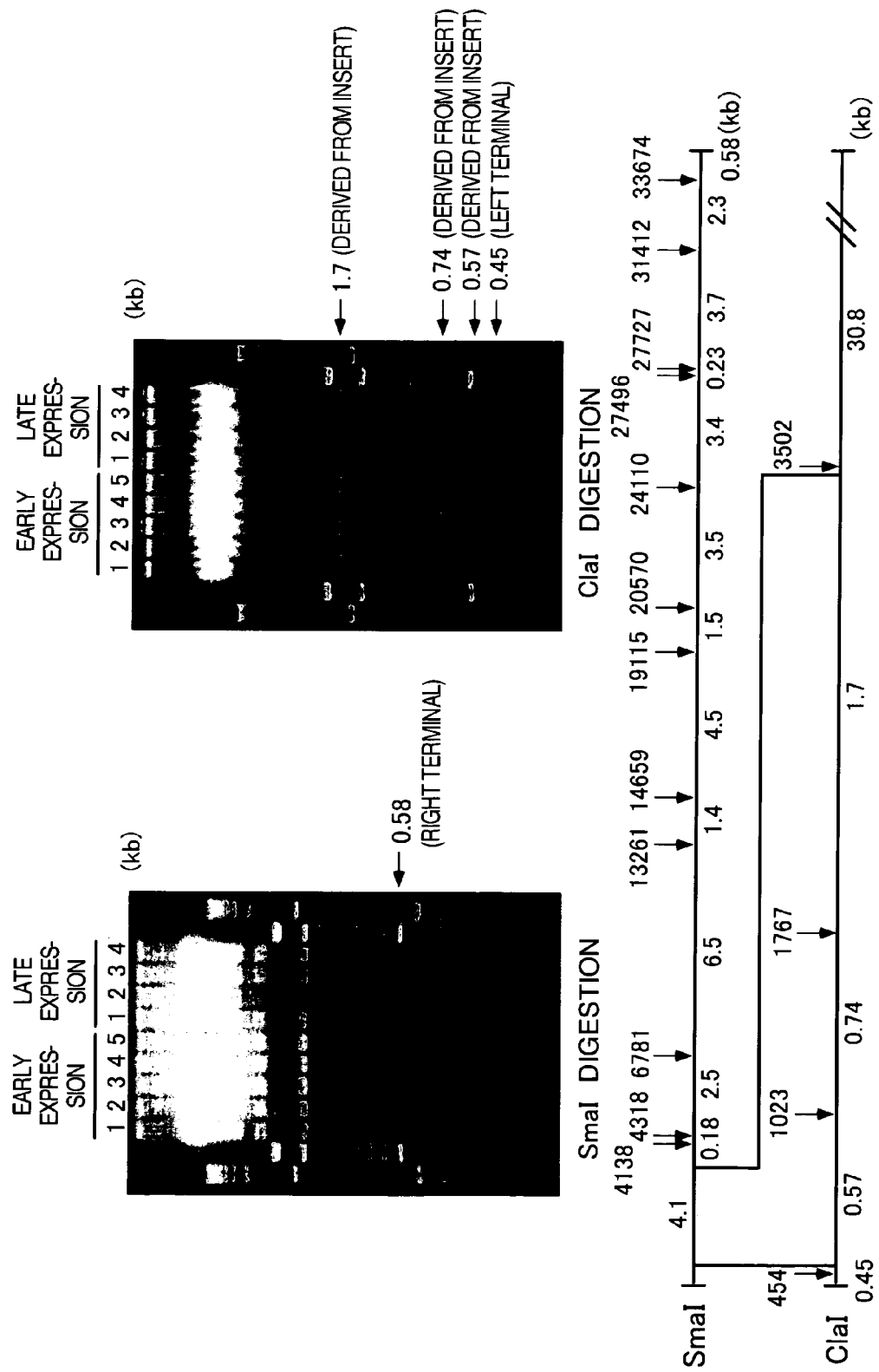

FIG. 7 shows the results of an experiment for confirming the structure of a recombinant adenovirus generated from a cell transformed with a cosmid vector pAxCARedEit. Five clones are selected from clones (early expression) in which the expression of RedE protein is confirmed 5 to 6 days after transfection and 4 clones are selected from clones (late expression) in which the expression of RedE protein is confirmed 8 to 10 days after transfection. The viral genome DNA of the clones is digested with SmaI or ClaI and analyzed.

The upper left figure and the upper right figure show the results of the agarose-gel electrophoresis of the DNA fragments digested with SmaI and ClaI, respectively. In the figures, the numeral on the gel represent the number of a clone. The lower figure schematically shows the positions of the restriction site on the recombinant adenoviral genome generated and the sizes of fragments digested with restriction enzymes. The numeral above an arrow is a nucleotide number of the each restriction site starting from the left terminal of the genome as being 1. The numeral under the line is a size (kb) of a fragment digested with a restriction enzyme.

Figure 8:
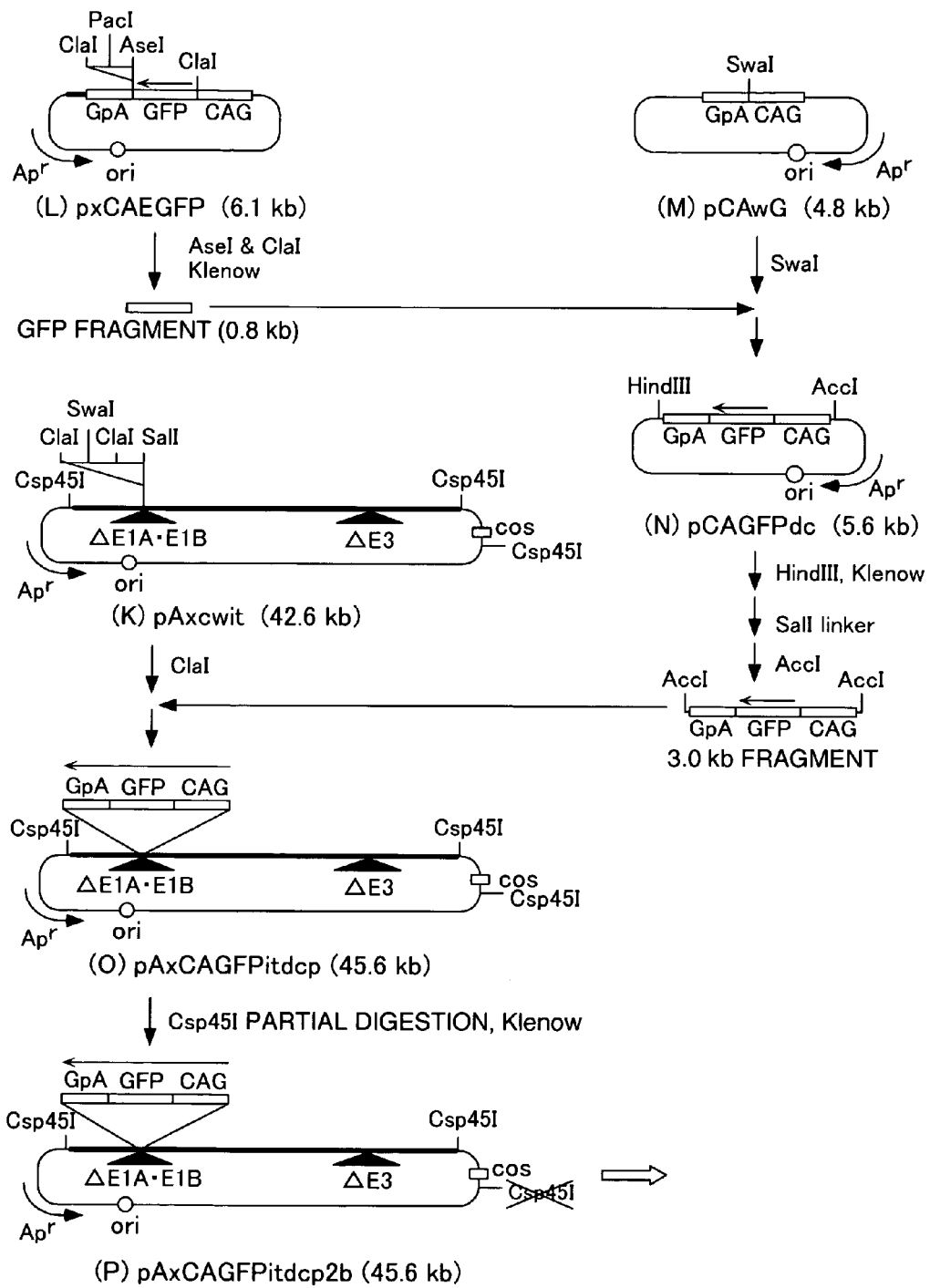
Figure 9:
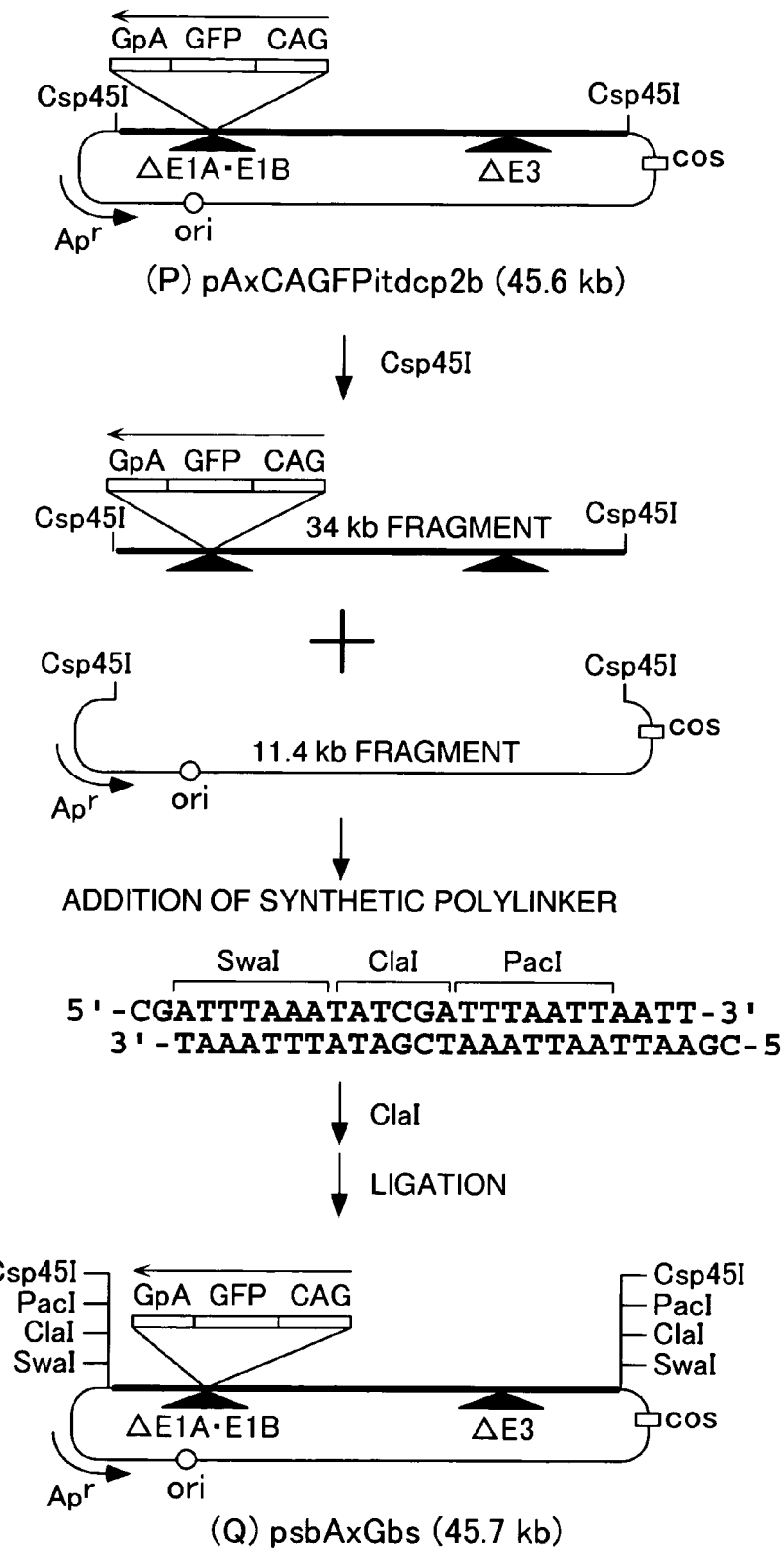

FIG. 8 is a schematic figure showing a method of constructing a cosmid vector according to the present invention having a multiple kinds of restriction enzyme recognition sites at both terminals of the adenoviral genome FIG. 9 is a schematic figure (continued from FIG. 8) showing a method of constructing a cosmid vector of the present invention having a multiple kinds of restriction enzyme recognition sites at both terminals of the adenoviral genome

BEST MODE FOR CARRYING OUT THE INVENTION

The present invention will be explained in detail below.

Note that, in this specification, a map unit (hereinafter referred to as "m.u." and 1 m.u. is equivalent to about 360 base pairs) is sometimes used to show the position of a gene on the adenoviral genome. The values are defined based on the adenovirus type 5. The genome structure of the adenovirus is known well. For example, the entire nucleotide sequence of the genome of human adenovirus type 2 has been registered with GenBank (Accession No. J01949) and that of human adenovirus type 5 with GenBank (Accession No. M73260). Therefore, if not otherwise specified, the positions of the gene encoded by the adenovirus are shown based on the adenovirus type 5 as an example. However, the adenovirus used in the specification is not limited to adenovirus Type 5.

(I) First Aspect of the Invention

The present invention provides a cosmid vector characterized by:

(1) containing an adenoviral genome having adenoviral inverted terminal repeat sequences each having a complete nucleotide sequence, (2) having a deletion in an adenovirus E1 gene region, and (3) containing a restriction enzyme recognition sequence not present in the adenoviral genome, on both sides of the adenoviral genome.

The adenoviral genome of item (1) refers to a double stranded linear DNA of a virus belonging to the family adenovirus, such as human adenovirus type 2 genome (GenBank Accession No. J01949), human adenovirus type 5 genome (GenBank Accession No. M73260). The adenoviral genome needs to have the complete sequence of the adenovirus inverted terminal repeat sequences as described below. However, in other regions, replacement, deletion and/or insertion of an appropriate nucleotide sequence may be occurred within the common knowledge of one skilled in the art as long as the recombinant adenoviral vector can maintain in its function.

The "adenovirus inverted terminal repeat sequences" (hereinafter, simply referred to as "ITR") are repetitive sequences inverted each other which are present at both ends of the adenoviral genome. The number of nucleotides varies depending upon the serotype of the adenovirus. For example, the ITR of the human adenovirus type 5 is 103 nucleotides long and type 2 is 102 nucleotides long.

Therefore, the phrase "an adenoviral genome having adenoviral inverted terminal repeat sequences each having a complete nucleotide sequence" means an adenoviral genome containing a complete nucleotide sequence of the ITR portion as is originally present in an adenovirus of each serotype.

In item (2), the "adenovirus E1 gene region" is a term collectively mentioning the E1A gene region located from 1.3 to 4.6 m.u. and the E1B gene region located from 4.6 to 11.2 m.u. In the E1 gene region, essential proteins for replication and expression of the adenovirus gene are encoded.

The phrase "having a deletion in an adenovirus E1 gene region" means that a whole or part of the nucleotide sequence of the E1 gene region is not present. The range of a deletion is not particularly limited as long as a protein encoded in the E1 gene region is not produced or a protein, if produced, does not function. Examples of a deletion in the E1 gene region include a deletion of 1.3 to 9.3 m.u. (Trapnell B. C., Advanced Drug Delivery Reviews, Vol. 12, 185-199. (1993) Elsevier Science Publishers B. V.).

In item (3), the term "both sides of the adenoviral genome" refers to positions flanking the adenoviral genome cloned in a plasmid vector or a cosmid vector. More specifically, on the left terminal ITR side, the position is opposite to the adenovirus packaging signal, whereas, on the right terminal ITR side, the position is opposite to the E4 gene promoter.

The restriction enzyme recognition sequence present on both sides of the adenoviral genome may be any restriction enzyme recognition sequence as long as it is not present in the adenoviral genome. Desirably, there can be mentioned a restriction enzyme recognition sequence consisting of 6 nucleotides, such as TTCGAA, which is a recognition sequence by restriction enzymes, Csp45I, BspT104I and BstBI. That is, according to a preferable aspect of the present invention, it is provided a cosmid vector containing TTCGAA on both sides of an adenoviral genome.

The cosmid vector of the present invention may have a single kind or a multiple kinds of restriction enzyme recognition sequences on both sides of an adenoviral genome. The case of having a multiple kinds of restriction site will be described later.

The adenoviral genome portion of the cosmid vector according to the present invention may have a further deletion of a gene except for the E1 gene region. Alternatively, the nucleotide sequence of the gene may have a partial replacement or insertion. Examples of a gene deletion except for the E1 gene region include deletions in the E3 gene region, pIX gene, the E4 gene region, and E2A gene. The term "deletion" used herein means the absence of a whole or part of a nucleotide sequence in any one of the genes and gene regions. The range of a deletion is not particularly limited as long as a protein encoded in the gene or gene region is not produced or a protein, if produced, does not function.

To insert a foreign gene such as cDNA or a promoter, it is preferable that a restriction enzyme recognition sequence not present in the adenoviral genome is present in a deletion site within the E1 gene region. As a preferable example of such a restriction enzyme recognition sequence, there can be mentioned a restriction enzyme recognition sequence generating a blunt end, such as the SwaI recognition sequence (ATT-TAAT). A sequence recognized by a restriction enzyme generating a blunt end is preferable because of the following reasons. One reason is that an insert fragment containing a foreign gene can be directly integrated into the cosmid vector simply by blunt-ending the insert fragment, without using a shuttle plasmid. The other reason is that a cosmid clone having no insert fragment can be removed by digesting the ligated fragment with the restriction enzyme (such as SwaI) after ligation of the cosmid vector with the insert fragment, consequently a desired cosmid clone having the insert can be efficiently obtained.

The deletion site within the E1 gene region may contain a promoter expressing a foreign gene. The promoter used herein refers to a nucleotide sequence required for transcribing a desired foreign gene. A promoter is not particularly limited as long as it functions in mammalian cells. For example, a promoter derived from an animal virus, a promoter derived from a mammalian cell, or a hybrid promoter of both may be used. Examples of such a promoter include a CAG promoter, EF-1α promoter, CMV promoter, SRα promoter, SV40 promoter, and RSV promoter. However, it is preferable to use a so-called high-level expression promoter, such as a CAG promoter (Niwa H. et. Al., Gene, Vol. 108, 193-200. (1991)), EF-1α promoter (Kim D. W. et. al. Gene, Vol. 91, 217-223. (1990)), and CMV promoter (Foecking M. K. et. al. Gene, Vol. 45, 101-105. (1986)).

The cosmid vector of the present invention contains at least a drug resistant gene, a replication origin, a spacer sequence and a COS region other than the adenoviral genome sequence. The drug resistant gene herein refers to a gene confering resistance against a drug toxic to *Escherichia coli*. Examples of such a drug resistant gene include an ampicillin resistant gene and a kanamycin resistant gene. The replication origin herein refers to a replication origin of a plasmid in *E. coli*.

The spacer sequence herein refers to a nucleotide sequence having no function by itself but contributing to adjusting the size of a whole cosmid vector. The spacer sequence is purposely inserted to increase the entire size of the cosmid vector larger than a constant size, thereby increasing the packaging efficiency of a cosmid vector in vitro. Examples of such a spacer sequence include an about 2 kb DNA fragment derived from plasmid pBR322 (Saito I. et. Al., Proc. Natl. Acad. Sci. USA, Vol. 83, 8664-8668. (1986)). It is preferable that three spacer sequences are arranged in tandem.

The COS region used herein refers to a nucleotide sequence to which a cohesive end of bacteriophage λ is ligated. For clear definitions of the drug resistant gene, the replication origin and the COS region, please refer to a text book such as Molecular Cloning, A Laboratory Manual., edited by T. Maniatis et al., Second edition (1989), Cold Spring Harbor Laboratory).

In the cosmid vector of the present invention, the drug resistant gene and the replication origin are desirably positioned between the left terminal ITR of the adenoviral genome and the spacer sequence. As the drug resistant gene and the replication origin are present between the left terminal ITR of the adenoviral genome and the spacer sequence in the cosmid vector of the present invention, after a desired foreign gene is inserted therein, it is possible to easily construct a plasmid in which a major part of the adenoviral genome, the spacer region and the COS region are removed (adeno removal) while the foreign gene insertion site is maintained to have the same nucleotide sequence as the cosmid vector.

To perform such an operation simply, it is desirable that the restriction enzyme recognition site, which is not present from the left side of the E1 gene region (ITR/packaging signal side) to the drug resistant gene and the replication origin, is added to the right side of the foreign gene insertion site of the E1 gene region (IVa2 gene side). Examples of such a restriction enzyme include SalI and NruI, whose recognition sites are present in the spacer sequence derived from the plasmid pBR322 mentioned above.

The drug resistant gene and the replication origin may be present in this order from the outside of the left terminal ITR of the adenoviral genome toward the right terminal ITR, or present in the reverse order. More specifically, the drug resistant gene, replication origin, the spacer sequence and the COS region may be contained in any one of the following orders <1> to <4> from the outside of the left terminal ITR of the adenoviral genome toward the right terminal ITR:

<1> The drug resistant gene, the replication origin, the spacer sequence, and the COS region;

<2> The replication origin, the drug resistant gene, the spacer sequence, and the COS region;

<3> The drug resistant gene, the replication origin, the COS region, and the spacer sequence;

<4> The replication origin, the drug resistant gene, the COS region, and the spacer sequence.

Of them, a cosmid vector containing the drug resistant gene, the replication origin, the spacer sequence, the COS region in this order is preferable.

Now, a method for constructing a cosmid vector according to the present invention will be described.

The cosmid vector of the present invention can be constructed from a cosmid vector having a major part of the adenoviral genome cloned therein. As an example, mention is made of a cosmid vector, pAxcw (pAdex1cw described in JP-A-8-308585, page 15 is identical with pAxcw), which contains a major part of the genome of human adenovirus type 5 excluding E1 and E3 gene regions but is deleted 33 bp from the left terminal and 198 bp from the right terminal (FIG. 3 (A)). First, cosmid vector pAxcw is digested with SalI and subjected to self-ligation, thereby constructing a plasmid (pxcws, FIG. 3 (B)) being deleted a major part of the adenoviral genome, but containing an about 430 bp portion from the left side (ITR/packaging signal side) of the E1 gene deletion site. In the plasmid pxcws, the deletion site of the left terminal portion of the adenoviral genome is only 33 bp from the left terminal of the genome. The deletion site can be repaired by synthesizing an oligo DNA fragment having the nucleotide sequence of the deletion site and inserting it to the deletion site. In this manner, it is possible to form a plasmid having a genome sequence containing the complete-form left terminal portion of the adenoviral genome. Note that, in synthesizing the oligo DNA, if a recognition sequence by a desired restriction enzyme is added adjacent to the left terminal of the adenoviral genome, it is possible to insert the recognition sequence of a restriction enzyme whose recognition site is not present in the adenoviral genome, to the left terminal of the adenoviral genome. The plasmid pyctcws (FIG. 3(D)) thus constructed has the complete-form left terminal ITR and a Csp45I site adjacent to the ITR. By replacing the EcoRI-SwaI fragment of plasmid pyctcws with the EcoRI-SwaI fragment of cosmid vector pAxcw, it is possible to obtain cosmid vector pAxcwith (FIG. 4(E)) with the left terminal completely repaired into complete form.

The deletion of 198 bp from the right terminal of the genome can be repaired in the same manner as in the left terminal by synthesizing several oligo DNAs divided into several portions of sequences corresponding to the deletion site and inserting the synthesized oligo DNA sequences into a plasmid at the right-terminal portion of the genome previously cloned in the plasmid. However, since the nucleotide sequence of the left terminal ITR is identical with that of the right terminal ITR, the deletion site of the right terminal can be repaired by taking advantage of this feature. Such a repair method will be explained in this specification. First, a plasmid pd1x (Saito I. et. al., J. Virol., Vol. 54, 711-719. (1985)) containing the adenovirus 5 type genome, from EcoRI site (at 75 map unit) to the proximity of the right terminal of the genome is used. A HindIII-BamHI fragment including about 1 kb from the right terminal of the genome is subcloned (plasmid pUAF97R (FIG. 4(F)). A HhaI-BamHI fragment of the plasmid pUAF97R is replaced with the HhaI-BamHI fragment (83 bp) of the plasmid pytcws to obtain a plasmid pUAF97Rct (FIG. 4(G)) having the right terminal in complete form. Finally, the right-side portion of the genome of the cosmid vector pAxcwith is replaced with the right-side portion of the genome of the plasmid pUAF97Rct to each other to obtain a cosmid vector pAxcwit (FIG. 5(K)) with both terminals completely repaired.

The cosmid vector of the present invention has various advantages and characteristics (1) to (5) (shown below) compared to conventional cosmid vectors and thus quite efficiently used in generating a recombinant adenoviral vector.
(1) A cosmid vector according to the present invention can efficiently generate an adenoviral vector by either the "cloned full-length genome introducing method" or the COS-TPC method (FIG. 1). In particular, the "cloned-genome introducing method" has a problem in that viruses are generated at a lower efficiency than a conventional method; however, the use of the cosmid vector of the present invention ensures a sufficient virus generation efficiency.

The method of generating an adenoviral vector will be explained more specifically. First, a recombinant adenovirus is generated by the "cloned-genome introducing method" using a cosmid vector according to the present invention having a foreign gene insert (desired gene) (FIG. 1(B)). In the case where a desired adenovirus is not obtained for the reason that when expression of the foreign gene inserted in a vector is toxic to the host cell, and in the case where a restriction enzyme recognition site for cleaving out the viral genome is present within the foreign gene, the cosmid vector according to the present invention is directly used as a cosmid cassette (cosmid vector) according to the conventional COS-TPC method (JP-A-8-308585) as it is, thereby obtaining a recombinant adenovirus (FIG. 1(A)). In the manner, a recombinant adenovitus can be efficiently generated by using the cosmid vector of the present invention even if any foreign gene is used.

(2) When the cosmid vector is used in the "cloned-genome introducing method", parent viral DNA is not required. Therefore, the recombinant adenovirus vector can be obtained at low cost. In addition, since a homologous recombination step required by a conventional method (COS-TPC method) is not required, almost all recombinant viruses generated are desired ones. Therefore, a desired virus vector having a desired viral gene can be easily generated without a screening step of a desired virus clone.

(3) When the cosmid vector of the present invention contains a drug resistant gene, a replication origin, a spacer sequence and a COS region in this order from the outside of the left terminal ITR of the adenoviral genome to the right terminal ITR, after a desired foreign gene is inserted into the cosmid vector of the present invention, it is possible to easily and advantageously construct a plasmid in which a major part of the adenoviral genome, the spacer region and the COS region are removed (adeno removal) while the foreign gene insertion site is maintained to have the same nucleotide sequence as the cosmid vector. By using of the adeno-removed plasmid, it is easily to sequence the junction of a foreign gene and a vector. Furthermore, when the cells are transformed with the adeno-removed plasmid, the expression of an inserted gene can be confirmed.

(4) A cosmid vector according to the present invention having a restriction enzyme recognition site (e.g., SwaI) generating a blunt end at the E1 gene deletion site has the advantage that an insert fragment containing a foreign gene can be directly integrated into the cosmid vector just by blunt-ending the insert fragment, without using a shuttle plasmid. Such a cosmid vector has another advantage. Since a cosmid clone not having insert fragment therein can be removed by digestion with SwaI after ligating the cosmid vector and the insert fragment, a desired cosmid clone having the insert can be obtained frequently.

(5) The cosmid vector of the present invention contains a restriction enzyme recognition sequence, which is not present in the adenoviral genome, at both terminals of the adenovirus genome. When the restriction enzyme is Csp45I (that is, the restriction enzyme recognition sequence is TTCGAA), there is the advantage that the cosmid vector can be easily and completely digested with the restriction enzyme before the cells are transformed. When the cosmid vector of the present invention is digested with a restriction enzyme, generally 30 μg of cosmid DNA is digested with 100 units of the restriction enzyme. Commercially available Csp45I from the company TOYOBO contains in an amount of 2500 units enzyme per package, it is possible to digest the cosmid vector of the present invention 25 times by a single package of Csp45I. On the other hand, commercially available restriction enzyme PacI (recognition sequence: TTAATTAA) from the company TOYOBO which is used to digest a plasmid and cosmid vector of the conventional "cloned-genome introducing method", is only contained in an amount of 50 units per package. Therefore, 2 packages of PacI are required to digest the cosmid vector of the present invention. In short, the number of the packed enzyme required for digesting the same amount of the cosmid vector differs by 50 times between Csp45I and PacI. Furthermore, the present inventors empirically found that a restriction enzyme containing a smaller amount of units per package tends to be difficult to completely digest substrate DNA compared to a restriction enzyme containing a larger amount of units per package even if the same units of enzyme is used. Therefore, Csp45I is advantageous over PacI since it easily attains complete digestion of the cosmid vector of present invention in a lower amount of enzyme compared to PacI.

Furthermore, the present invention provides a method for generating a recombinant adenoviral vector using the cosmid vector of the present invention. The method for generating an adenoviral vector according to the present invention comprises the following steps (1) and (2):
(1) digesting the cosmid vector of the present invention with a restriction enzyme; and
(2) transforming the cells with the cosmid vector digested with the restriction enzyme in the step (1).

The restriction enzyme used in the step (1) is one capable of digesting the restriction enzyme recognition sequence not present within the adenoviral genome but present on both sides of the adenoviral genome, more specifically, a restriction enzyme recognizing a sequence of TTCGAA, such as Csp45I, BspT104I or BstBI.

The cells used in the step (2) are not particularly limited as long as they can express adenovirus E1 gene and are suitable for propagating the adenovirus. Examples of such cells include cell strain 293 cells (ATCC CRL1573) derived from the human embryonic kidney cells.

Next, a method for generating a recombinant adenoviral vector according to the present invention will be described below.

First, cells such as 293 cells are transfected with a cosmid vector. A methods to transfect the cells is not particularly limited and a conventional method such as a calcium phosphate co-precipitation method, ripofection method, DEAE-dextran method, and electroporation method may be used. A recombinant adenoviral vector is generated by culturing a transformed cell. The virus generated is desirably cloned. A cloning method is not particularly limited. There is a method of isolating a plaque formed by proliferations of a virus thus generated and a method of serially diluting transformed cells and seeding them into a 96 well plate. Since almost all the generated viruses are desired virus clones, any clone may be chosen and used as a desired virus; however, it is rather desirable to use a clone that is confirmed to have a desired viral structure by a restriction analysis. The cosmid vector of the present invention can be used as a cosmid cassette (cosmid vector) in accordance with a conventional COS-TPC method to generate a recombinant adenoviral vector. In this case, the above-mentioned step (1) of digesting a cosmid vector with a restriction enzyme is not required.

The present invention also provides a reagent for constructing a recombinant adenoviral vector, containing a cosmid vector according to the present invention as a component. The reagent of the present invention to be provided contains a cosmid vector dissolved in water or in an appropriate buffer. The buffer is not particularly limited as long as it is suitable for dissolving and stabilizing DNA. Desirably, TE buffer is used.

Furthermore, the reagent to be provided may contain a cosmid vector according to the present invention in the circular form or a cosmid vector previously digested with a restriction enzyme such as SwaI.

The reagent of the present invention may be included as a component of a kit for constructing a recombinant adenovirus. Examples of other components of the kit may include various reagents essentially for constructing a recombinant adenovirus such as restriction enzyme(s), restriction enzyme reaction buffer, DNA ligase, ligase reaction buffer, and adenoviral genome DNA with terminal proteins (DNA-TPC) previously digested with a restriction enzyme(s). As the restriction enzyme(s), it may be mentioned that i) a restriction enzyme for digesting a restriction site at both terminals of the adenoviral genome, such as Csp45I, BspT104I or BstBI and/or ii) a restriction enzyme for digesting a restriction site present in the E1 gene deletion site (for example, SwaI). Examples of DNA-TPC previously digested with a restriction enzyme include DNA-TPC obtained by digesting the genomic DNA of adenovirus Ad5-dlX (Miyake S. et. Al., Proc. Natl. Acad. Sci. USA, Vol. 93, 1320-1324. (1996)) with EcoE22I, and DNA-TPC obtained by digesting the genomic DNA of recombinant adenovirus AxCAwt (Kanegae Y. et. al., Nucleic acid Res., Vol. 23, 3816-3821 (1995)) with EcoE22I and ClaI.

(II) Second Aspect of the Present Invention

As is explained in the above, to solve a problem associate with the case where a restriction site for excising a viral genome from the cosmid vector is present within a foreign gene, the cosmid vector of the present invention may be used as a conventional cosmid vector of the COS-TPC method. As another means, the present inventors found it useful to use of a cosmid vector having a multiple kinds of restriction enzyme recognition sequences for cleaving out a viral genome. More specifically, a vector having a single kind of restriction enzyme recognition sequence at both terminals of the adenoviral genome is only known in the art and this becomes a common-sense. However, the present inventors found for the first time that a multiple kinds of restriction enzyme recognition sequences can be introduced. In principle, such a technique for introducing a multiple kinds of restriction enzyme recognition sites can be applied not only to a cosmid vector but also a plasmid vector.

Accordingly, the present invention provides a cosmid vector or plasmid vector characterized by:
(1) containing an adenoviral genome sequence having adenoviral inverted terminal repeat sequences each having a complete nucleotide sequence,
(2) having a deletion in an adenovirus E1 gene region, and
(3) containing a multiple kinds of restriction enzyme recognition sequences not present in the adenoviral genome, on both sides of the adenoviral genome.

The features (1) to (3) are the same as described in the first aspect of the present invention. Therefore, the feature (3) "containing a multiple kinds of restriction enzyme recognition sequences" will be explained in detail.

Based on the precondition that the same restriction enzyme recognition sequences are present at both the left side and the right side of the adenoviral genome, two or more kinds of restriction enzyme recognition sequences may be present.

Any specific restriction enzyme recognition sequence may be used as long as it is not present within the adenoviral genome. For example, it is mentioned that a cosmid vector or plasmid vector comprising at least two kinds of restriction enzyme recognition sequences selected from
(a) TTCGAA recognized by a restriction enzyme such as Csp45I, BspT104I, and BstBI (hereinafter sometimes simply referred to as a "recognized by a restriction enzyme Csp45I"),
(b) TTAATTAA recognized by a restriction enzyme PacI, and
(c) ATCGAT recognized by a restriction enzyme ClaI or BspDI (hereinafter referred to as "recognized by a restriction enzyme ClaI").

Preferably, it may be mentioned that a cosmid vector or plasmid vector at least containing (a) TTCGAA recognized by a restriction enzyme Csp45I and (b) TTAATTAA recognized by a restriction enzyme PacI, and a cosmid vector or a plasmid vector containing at least (a) TTCGAA recognized by a restriction enzyme Csp45I and (c) ATCGAT recognized by a restriction enzyme ClaI.

As described above, the restriction enzyme recognition sequence present on both sides of an adenoviral genome may not be one. Two or more kinds of restriction enzyme recognition sequences may be present. Specifically, it is mentioned that a cosmid vector or a plasmid vector having two kinds of restriction enzyme recognition sequences, a cosmid vector or plasmid vector having three kinds of restriction enzyme recognition sequences, and a cosmid vector or plasmid vector having four kinds of restriction enzyme recognition sequences.

When two kinds of restriction enzyme recognition sequences which are not present in the adenoviral genome, are present on both sides of the adenoviral genome, it may be mentioned that a cosmid vector or plasmid vector containing two kinds of restriction enzyme recognition sequences selected from (a) TTCGAA recognized by a restriction enzyme Csp45I and (b) TTAATTAA recognized by a restriction enzyme PacI and (c) ATCGAT recognized by a restriction enzyme ClaI.

According to a preferable aspect, it may be mentioned that a cosmid vector or a plasmid vector containing (a) TTCGAA recognized by a restriction enzyme Csp45I and (b) TTAATTAA recognized by a restriction enzyme PacI. In this case, the order of two kinds of restriction enzyme recognition sequences is not particularly limited and specifically the following four arrangements are exemplified.

(A) The PacI recognition sequence-the Csp45I recognition sequence-the adenoviral genome-the Csp45I recognition sequence-the PacI recognition sequence-the vector sequence;
(B) The Csp45I recognition sequence-the PacI recognition sequence-the adenoviral genome-the PacI recognition sequence-the Csp45I recognition sequence-the vector sequence;
(C) The PacI recognition sequence-the Csp45I recognition sequence-the adenoviral genome-the PacI recognition sequence-the Csp45I recognition sequence-the vector sequence;
(D) The Csp45I recognition sequence-the PacI recognition sequence-the adenoviral genome-the Csp45I recognition sequence-the PacI recognition sequence-vector sequence.

Of them, the preferable order is the PacI recognition sequence-the Csp45I recognition sequence-the adenoviral genome-the Csp45I recognition sequence-the PacI recognition sequence. When the restriction enzyme sites at which a viral genome to be excised are both the Csp45I and the PacI recognition sequences, the restriction enzyme recognition sequences that can be used in cloning of a foreign gene into the cosmid vector of the present invention are SwaI recognition sequence and ClaI recognition sequence.

As another preferable aspect of a cosmid vector and a plasmid vector containing two kinds of restriction enzyme recognition sequences, it may be mentioned that a cosmid vector and a plasmid vector containing (a) TTCGAA recognized by a restriction enzyme Csp45I and (c) ATCGAT recognized by a restriction enzyme ClaI. The order of the two kinds of restriction enzymes are not particularly limited, the following (A) to (D) may be exemplified.

(A) The ClaI recognition sequence-the Csp45I recognition sequence-the adenoviral genome-the Csp45I recognition sequence-the ClaI recognition sequence-the vector sequence;
(B) The Csp45I recognition sequence-the ClaI recognition sequence-the adenoviral genome-the ClaI recognition sequence-the Csp45I recognition sequence-the vector sequence;
(C) The ClaI recognition sequence-the Csp45I recognition sequence-the adenoviral genome-the ClaI recognition sequence-the Csp45I recognition sequence-the vector sequence;
(D) The Csp45I recognition sequence-the ClaI recognition sequence-the adenoviral genome-the Csp45I recognition sequence-the ClaI recognition sequence-the vector sequence.

Of them, the desirable order is the ClaI recognition sequence-the Csp45I recognition sequence-the adenoviral genome-the Csp45I recognition sequence-the ClaI recognition sequence. When the restriction enzyme recognition sequences for excising a viral genome are both the Csp45I and the ClaI recognition sequences, the SwaI recognition sequence and the PacI recognition sequence can be used as the restriction enzyme recognition sequences for cloning of a foreign gene into the cosmid vector of the present invention. When three kinds of restriction enzyme recognition sequences which are not present in the adenoviral genome, are present on both sides of the adenoviral genome, it may be mentioned that a cosmid vector or plasmid vector containing (a) TTCGAA recognized by a restriction enzyme Csp45I,
(b) TTAATTAA recognized by a restriction enzyme PacI.
(c) ATCGAT recognized by a restriction enzyme ClaI.

The oder of these three kinds of restriction enzyme recognition sequences is not particularly limited, and any combination (36 cases) may be used as same as mentioned in the case of two kinds of restriction enzyme recognition sequences. As an example, it may be mentioned that a cosmid vector having the order of the ClaI recognition sequence-the PacI recognition sequence-the Csp45I recognition sequence-the adenoviral genome-the CsP45I recognition sequence-the PacI recognition sequence-the ClaI recognition sequence-the vector sequence. In this case, as a restriction enzyme recognition sequence for cloning of a foreign gene, the SwaI recognition sequence can be used.

In the cosmid vector according to the present invention having a multiple kinds of restriction enzyme recognition sequences for excising out a viral genome, even if the cosmid vector is digested not only at a restriction enzyme recognition sequence closest to the adenoviral genome but also at a restriction recognition sequence that is 20 nucleotides distant from a terminal of the viral genome, a desired recombinant adenoviral vector can be sufficiently obtained. This is apparent from Example 7.

Note that Example 7 is a model system used for showing that an adenoviral vector can be obtained even if a cosmid is digested at a restriction enzyme recognition sequence distant from a terminal of an adenoviral genome and the cosmid vector contains the SwaI recognition sequence, ClaI recognition sequence, PacI recognition sequence, and Csp45I recognition sequence as restriction enzyme recognition sequences for excising a viral geneme. Example 7 thus shows, even in the case where four kinds of restriction enzyme recognition sequences are present, a desired adenoviral vector can be obtained also by digesting the cosmid at the most distant restriction enzyme recognition sequence from both sides of the adenoviral genome. In a cosmid vector for inserting a foreign gene in practice, it is desirable to remove the SwaI recognition sequence from the restriction enzyme recognition sequences for excising a viral genome and, instead, to insert the SwaI recognition sequence to the E1 gene deletion site for cloning of the foreign gene.

As described above, application of a vector having a multiple kinds of restriction enzyme recognition sequences for excising the adenoviral genome is not limited to a cosmid vector. Such a vector is applicable to a plasmid vector, in other words, generally applicable to a method ("cloned-genome introducing method") based on the principle for generating an adenovirus, that is, by transforming cells with a plasmid vector and a cosmid vector having the full-length adenoviral genome after digestion with a restriction enzyme to excise the viral genome.

For example, in a plasmid vector (Adeno-X™ Expression System sold by Clonetech Laboratories, Inc.) for use in generating recombinant adenovirus based on the method of the present invention, the PacI recognition sequence is used for cleaving the viral genome. However, when the PacI recognition sequence is present within a foreign gene inserted in the vector, it is instructed to digest partially with PacI. However, it is generally difficult to determine the conditions for partial digestion with a restriction enzyme. The rate of DNA cleaved at desired sites by partial digestion is extremely low compared to complete digestion. Therefore, even if the plasmid vector for generating adenovirus mentioned above is partially digested with PacI, the ratio of DNA not cleaved at the PacI site within a foreign gene but cleaved at the PacI site of both terminals of the adenoviral genome is extremely low. Therefore, even if cells are transformed with the DNA mentioned above, the possibility of obtaining a desired recombinant adenoviral vector is extremely low.

In this case, if it is used a plasmid vector of the present invention having not only the PacI recognition sequence but also recognition sequences of second and third restriction enzymes for excising adenoviral genome, the plasmid vector can be digested with the second or third restriction enzyme without inefficient partial digestion, as a result a desired adenoviral vector can be efficiently generated. Such restriction enzyme recognition sequences are not particularly limited as long as they are not present in the adenoviral genome portion. Examples of such a sequence are the same as described above. The preferable plasmid vector to be mentioned has at least two kinds of restriction enzyme recognition sequences selected from the PacI recognition sequence (TTAATTAA), the Csp45I recognition sequence (TTCGAA), and the ClaI recognition sequence (ATCGAT).

In a vector (cosmid vector, plasmid vector) according to the present invention containing a multiple kinds of restriction enzyme recognition sequences not present in the adenoviral genome, on both sides of the adenoviral genome, the restriction enzyme recognition sequences not present in the adenoviral genome are preferable present in the E1 gene deletion site so as to insert a foreign gene such as cDNA and a promoter, as described in the first aspect of the present invention. Such a restriction enzyme recognition sequence is preferably one capable of generating a blunt end, more specifically, the SwaI recognition sequence (ATTTAAT).

The E1 gene deletion site may contain a promoter for expressing a foreign gene. The promoter used herein refers to a nucleotide sequence required for transcription of a desired foreign gene. Any promoter may be used without particular limitation as long as it functions in a mammalian cell. Examples of such a promoter include a promoter derived from an animal virus, a promoter derived from a mammalian cell, and a hybrid of both promoters. Specific examples of such a promoter include the CAG promoter, the EF-1a promoter, the CMV promoter, the SRα promoter, the SV40 promoter, and the RSV promoter. However, it is preferable to use a promoter known to be responsible for high-level expression, such as the CAG promoter (Niwa H. et. Al., Gene, Vol. 108, 193-200. (1991)), the EF-1α promoter (Kim D. W. et. al. Gene, Vol. 91, 217-223. (1990)) and the CMV promoter (Foecking M. K. et. al. Gene, Vol. 45, 101-105. (1986)).

In the case where a vector according to the second aspect of the present invention is a cosmid vector, the vector contains at least a drug resistant gene, a replication origin and the COS region other than the adenoviral genome sequence. A spacer sequence is also desirably contained. These components are the same as described in the first aspect of the present invention.

In the cosmid vector, the drug resistant gene and the replication origin are desirably positioned between the left terminal ITR of the adenoviral genome and the spacer sequence. More specifically, because of the presence of the drug resistant gene and the replication origin between the left terminal ITR of the adenoviral genome and the spacer sequence, it is possible to easily construct a plasmid in which a major part of the adenoviral genome, the spacer region and the COS region are removed (adeno removal) while the foreign gene insertion site is maintained to have the same nucleotide sequence as the cosmid vector into which a desired foreign gene has been previously inserted.

To perform such an operation simply, it is desirable that the restriction enzyme recognition site not present in the region from the left side (ITR/packaging signal) of the E1 gene region to the drug resistant gene or the replication origin, is added to the right side (IVa2 gene side) of the foreign gene insertion site of the E1 gene region. Examples of such a restriction enzyme include SalI and NruI, whose recognition sites are also present in the spacer sequence derived from the plasmid pBR322 mentioned above.

The drug resistant gene and the replication origin may be present in this order from the outside of the left terminal ITR of the adenoviral genome toward the right terminal ITR, or present in the reverse order. More specifically, the drug resistant gene, the replication origin, the spacer sequence and the COS region may be contained in any one of the following orders <1> to <4> from the outside of the left terminal ITR of the adenoviral genome toward the right terminal ITR:

<1> The drug resistant gene, the replication origin, the spacer sequence, the COS region;

<2> The replication origin, the drug resistant gene, the spacer sequence, the COS region;

<3> The drug resistant gene, the replication origin, the COS region, the spacer sequence;

<4> The replication origin, the drug resistant gene, the COS region, the spacer sequence.

Of them, a cosmid vector containing a drug resistant gene, the replication origin, the spacer sequence, the COS region in this order is preferable.

A recombinant adenoviral vector can be generated by using a cosmid vector according to the second aspect of the present invention as mentioned above. This is the same as explained in the first aspect of the present invention. More specifically, the following steps (1) and (2) are included.

(1) digesting a cosmid vector according to the present invention with a restriction enzyme.

(2) transforming a cell with the cosmid vector digested with a restriction enzyme in the step (1).

The restriction enzyme used in the step (1) is one capable of digesting the restriction enzyme recognition sequence not present within the adenoviral genome but present on both sides of the adenoviral genome, more specifically, Csp45I, BspT104I or BstBI is used for digesting at the TTCGAA sequence present on both sides of the adenoviral genome; PacI for digesting at the TTAATTAA sequence, and ClaI or BspDI for digesting at the ATCGAT sequence.

The cells used in the step (2) are not particularly limited as long as they are suitable for expressing adenovirus E1 gene and propagating adenovirus. Examples of such cells include cell strain 293 cells (ATCC CRL1573) derived from the human embryonic kidney.

A method for generating a recombinant adenoviral vector using a cosmid vector and the cells are the same as described in the first aspect of the present invention. Furthermore, when a plasmid vector is used as the vector, a recombinant adenoviral vector can be generated in the same manner as in the cosmid vector.

These cosmid vectors and plasmid vectors may be contained as components of a reagent for generating a recombinant adenoviral vector. Specific aspect of these is the same as described in the first aspect of the present invention above.

EXAMPLES

Now, the present invention will be explained in detail below by way of examples, which will not be construed as limiting the scope of the present invention. It goes without saying that ordinary modification can be made within the technical field of the present invention. Note that various manipulations for treating phages, plasmids, DNA, enzymes, *Escherichia coli*, and cultured cells are performed in accordance with a method described in Molecular Cloning, A Laboratory Manual edited by T. Maniatis et al., Second edition (1989), Cold Spring Harbor Laboratory, if not otherwise specified.

Example 1

Construction of a Cosmid Vector having Adenoviral Genome with the Complete Sequence of both Terminals <1> The cosmid vector pAxcw (the cosmid pAdex1cw described in JP-A-8-308585, page 15, is identical with the cosmid pAxcw) contains a major part of the genome of human adenovirus type 5 but does not contain E1 and E3 gene regions and is devoid of 33 bp from the left terminal of the adenoviral genome and 198 bp from the right terminal (cosmid vector both terminals deletion type) (see FIGS. 2A and 3(A)). The cosmid vector pAxcw was digested with SalI and was self-ligated to obtain the plasmid pxcws (3.1 kb, FIG. 3(B)) which was just containing about 0.4 kb portion from the left terminal of the adenoviral genome and the other portion of the adenoviral genome was removed.

<2> To construct a plasmid containing the complete sequence of the left terminal ITR, the following manipulation were performed.

(a) The plasmid pxcws was digested with BamHI and BsrGI to obtain a DNA fragment of about 2.9 kb containing the ori.

(b) The plasmid pxcws was digested with HaeIII and BsrGI to obtain a DNA fragment of about 162 bp (b) containing ITR.

(c) The following two oligo DNA fragments containing left terminal portion of the adenovirus type 5 genome, which were designed that one ends was able to lignite to a BamHI digestion fragment and the other end was blunt end after annealing, were synthesized. After phospholyation of the 5'-end, these fragment were annealed.

(Sequence ID 1)
5'-gatccgcatgCATCATCAATAATATACCTTATTTTGGATTGAAG-3'

(Sequence ID No. 2)
5'-CTTCAATCCAAAATAAGGTATATTATTCATGATGcatgcg-3'

(Capital letters indicate the nucleotide sequence of adenoviral genome portion)

Three fragments (a)(b)(c) were ligated to construct a plasmid pytcw (3.1 kb, FIG. 3(C)) containing the complete sequence of the left terminal ITR.

<3> To introduce a Csp45I site into the plasmid pytcw, the following manipulations were performed. The plasmid pytcw was digested with EcoT22I and the 3' protruding end was blunted by Klenow enzyme. A 5'-end phosphorylated synthetic linker (5'-TGTTCGAACA-3') containing a Csp45I recognition sequence was ligated to the above DNA fragment to obtain a plasmid pyctcws (3.1 kb, FIG. 3(D)) inserting a single linker.

<4> The plasmid pyctcws was digested with SwaI and EcoRI to prepare a DNA fragment of 482 bp (a) containing the complete sequence of the left terminal ITR and a packaging signal. On the other hand, a cosmid vector pAxcw was digested with EcoRI to prepare a DNA fragment of about 18 kb (b) containing the ori and the COS region. Also, the cosmid vector pAxcw was digested with SwaI and EcoRI to prepare a DNA fragment of about 24 kb (c) not containing the COS region. Three fragments (a)(b)(c) were ligated to obtain a cosmid vector pAxcwith (42.5 kb, FIG. 4(E)). The cosmid vector pAxcwith is devoid of 198 bp sequence of right terminus including ITR but has complete sequence of the ITR at the left terminal side.

<5> A plasmid pd1x contains the region from the EcoRI site at 76 map unit to the proximity of the right terminal of the adenovirus type 5 genome (Saito I. et. al., J. Virol., Vol. 54, 711-719. (1985)). The plasmid pd1x was digested with HindIII and BamHI to prepare a DNA fragment of about 1 kb containing the right-terminal side portion of the adenoviral genome. The DNA fragment was inserted between the HindIII site and the BamHI site within the multicloning site of the plasmid pUC19 to obtain a plasmid pUAF97R (3.7 kb, FIG. 4(F)).

<6> The plasmid pUAF97R was digested with BamHI and Aor51HI to prepare a DNA fragment of about 3.3 kb (a) containing the ori. The plasmid pUAF97R was digested with Aor51HI and HhaI to prepare a DNA fragment of 375 bp (b) not containing the ori. On the other hand, the plasmid pyctcws constructed in step <2> was digested with BamHI and HhaI to obtain a DNA fragment of 83 bp (c) containing a part of ITR. The three fragments (a)(b)(c) were ligated to obtain a plasmid pUAF97Rct (3.7 kb, FIG. 4(G)).

<7> The 713 bp fragment between the BstEII and BamHI site of the plasmid pUAF97Rct was substituted with the region between the BstEII and BamHI site of plasmid pd1x to obtain a plasmid pd1xct (9.0 kb, FIG. 5(H)) having the complete sequence of the right terminal ITR.

<8> A cosmid vector pAx4w (FIG. 5(I)) has a foreign gene insertion site between the upstream region of adenovirus E4 gene and the right terminal ITR (Miyake S. et. Al., Proc. Natl. Acad. Sci. USA, Vol. 93, 1320-1324. (1996)). The cosmid pAx4w was digested with EcoRI and BamHI to obtain a DNA fragment of about 11 kb containing the ori and the COS region. On the other hand, plasmid pd1xct was digested with EcoRI and BamHI to obtain a DNA fragment of 6.7 kb not containing the ori. Both fragments were ligated to obtain a plasmid pcd1xct (18.1 kb, FIG. 5(J)).

<9> A cosmid vector pAxcwith (constructed in step <4>) was digested with EcoRI to prepare a DNA fragment of about 24.6 kb containing the left terminal ITR. The DNA fragment was inserted into the EcoRI site of the plasmid pcd1xct to obtain a cosmid vector pAxcwit (42.6 kb, FIG. 5(K)) having the complete sequence of both the left terminal ITR and right terminal ITR.

19

Example 2

Construction of a Cosmid Vector having an
Expression Unit Inserted therein (1) Construction of a Cosmid Vector having an Expression Unit of a Red Fluorescent Protein Derived from a Coral A cosmid vector pAxCAwt (FIG. 6(A)) has the same nucleotide sequence of adenoviral genome (both terminals deletion type) as that of the cosmid vector pAxcw and has a CAG promoter (Niwa H. et. Al., Gene, Vol. 108, 193-200, (1991) and Japanese Patent No. 2824434) inserted in the E1 gene deletion site in the left side orientation (i.e., the reverse direction of E1 gene transcription direction) (Kanegae Y. et. al., Nucleic acid Res., Vol. 23, 3816-3821 (1995)). The cosmid vector pAxCAwt has a SwaI site for inserting a foreign gene, between the CAG promoter and a polyadenylation signal.

A gene fragment encoding the red fluorescent protein (RedE) derived from a coral was prepared from a commercially available plasmid, pCMV-DsRed-Express (the company Clonetech Laboratories, Inc). The plasmid pCMV-DsRed-Express was digested with NotI and Aor51HI, and was blunt-ended by Klenow enzyme to obtain a DNA fragment of 713 bp containing a RedE gene. The DNA fragment was inserted into the SwaI site of the vector pAxCAwt to obtain a cosmid vector pAxCARedE (45.5 kb, both terminals deletion type, see FIG. 2A) having a RedE expression unit inserted therein.

Subsequently, the cosmid vector pAxCARedE was digested with SalI and PmeI and blunt-ended by Klenow enzyme to obtain a DNA fragment of about 3 kb containing the RedE expression unit, which was then inserted into the SwaI site of the cosmid vector pAxcwith constructed in Example 1 to obtain a cosmid vector pAxCARedEith (45.5 kb, the left terminal complete type, see FIG. 2B). Similarly, a DNA fragment containing a RedE expression was inserted into the SwaI site of the cosmid vector pAxcwit to obtain a cosmid vector pAxCARedEit (45.5 kb, both terminals complete type, see FIG. 2C).

(2) Construction of a Cosmid Vector Having an Expression Unit of a Green Fluorescent Protein Derived From a Jellyfish A plasmid vector pxCAEGFP has a gene of the green fluorescent protein (GFP) derived from jellyfish ligated downstream of the CAG promoter (Nakano M. et. al., Nucleic acid Res., Vol. 29, e40 (2001)). The plasmid pxCAEGFP was digested with SalI and PmeI and blunt-ended by Klenow enzyme to obtain a DNA fragment of about 3.1 kb containing a GFP expression unit, which was further inserted into the SwaI site of the cosmid vector pAxcw (both terminals deletion type) to obtain a cosmid vector pAxCAGFP (45.6 kb). Similarly, a DNA fragment containing a GFP expression unit was inserted into the SwaI site of the cosmid vector pAxcwit (both terminals complete type) to obtain a cosmid vector pAxCAGFPit (45.6 kb).

(3) Construction of a Cosmid Vector for Inserting a Any Gene Downstream of the CAG Promoter.

A cosmid vector pAxCAwt (both terminals deletion type, see FIG. 6 (A)) was digested with BsrGI and BstZ17I to obtain a DNA fragment of about 5.1 kb (a) containing the CAG promoter. On the other hand, a cosmid vector pAxcwit (both terminals complete type, FIG. 6(B)) was digested with BsrGI and SrfI to obtain a DNA fragment of about 18 kb (b) containing the ori and the COS region. Cosmid vector pAxcwit was digested with BstZ17I and SrfI to obtain a DNA fragment of about 22 kb (c) not containing the ori. The three fragments (a)(b)(c) were ligated to obtain a cosmid vector pAxCAwtit (45.0 kb, FIG. 6(C)). The cosmid vector pAx-

20

CAwtit has the same nucleotide sequence as that of the cosmid vector pAxCAwt (both terminals deletion type) except for both terminals of the adenoviral genome and has a SwaI site or a ClaI site between the CAG promoter and the polyadenylation for inserting a foreign gene.

Example 3

Construction of a Plasmid Removing the Majority of the Adenoviral Genome and Confirmation of the Expression of an Inserted Gene (1) Construction of a Plasmid Removing the Majority of the Adenoviral Genome Cosmid vectors pAxCARedEit and pAxCAGFPit constructed in Example 2 have restriction enzyme SalI site and NruI site immediately upstream of the CAG promoter and within the spacer region. Therefore, a plasmid removing the majority of the adenoviral genome (containing about 0.4 kb from the left terminal) can be constructed by self-ligation of these cosmid vectors after digestion with the restriction enzyme.

After pAxCARedEit was digested with SalI, the DNA fragment was self-ligated. Then, *Escherichia coli* DH5 was transformed with the self-ligated DNA to obtain plasmid pxCARedEit (6.1 kb) removing the majority of the adenoviral genome and the spacer region.

Similarly, the cosmid vector pAxCAGFPit was digested with SalI and self-ligated to obtain plasmid pxCAGFPit (6.2 kb).

(2) Confirmation of Expression of the Red Fluorescent Protein

To confirm whether the expression unit of red fluorescent protein (RedE) derived from coral was accurately integrated in the cosmid vector pAxCARedEit, cells were transformed with the plasmid pxCARedEit constructed in the Step (1). In this manner, the expression of RedE was confirmed.

First, 3 µg of plasmid pxCARedEit and 9 µl of a transfection reagent, TransFast (registered trade mark, manufactured by Promega) were added to 1 ml of the Dulbecco's modified Eagle medium (DMEM medium) containing no serum. After the mixture was stirred well and incubated at room temperature for 15 minutes. The culture medium was removed from the confluent cultured 293 cells in a 6-well plate coated with collagen and all the mixture of the plasmid and the reagent were added to the culture plate and cultured at 37° C. for one hour. Thereafter, 2 ml of DMEM medium supplemented with 5% FCS was added to the plate, and cells were cultured for 16 hours. After the medium was replaced to the fresh medium cells was further cultured. Two days after the transfection the red fluorescence was observed in numerous transfected cells by a fluorescent microscope (at excitation wavelength: 558 nm/radiation wavelength: 583 nm). As a result, it was confirmed that the RedE expression unit was accurately integrated in the cosmid vector pAxCARedEit.

Example 4

Generation of a Recombinant Adenoviral Vector by the Transfection with a Cosmid Vector alone A cosmid vector pAxCARedE (both terminals deletion type), pAxCARedEith (left terminal complete type), pAxCARedEit (both terminals complete type), pAxCAGFP (both terminals deletion type), pAxCAGFPit (both terminals complete type) constructed in Example 2, were prepared each in a large amount. 30 µg of each cosmid DNA was digested with Csp45I (TOYOBO) at 37° C. for 2 hours. An aliquot of each reaction mixture was subjected to agarose gel electrophoresis, and the complete digestion of DNA was confirmed, then the reaction mixture was extracted with phenol/chloroform, subsequently with chloroform twice and precipitated with ethanol. After the ethanol precipitation, DNA was dissolved in 60 µl of TE buffer. An aliquot (1 µl) was subjected to agarose gel electrophoresis. DNA concentration was calculated by comparing the density of a 1.5 kb-band with that of a already-known concentration DNA and subjected to transformation.

First, 10 µg of cosmid DNA previously digested with Csp45I and 30 µl of a transfection reagent, TransFast (registered trade mark) were added to 2 ml of the Dulbecco's modified Eagle medium (DMEM medium) containing no serum. After the mixture was stirred well and incubated at room temperature for 15 minutes. Note that the cosmid pAxCARedEit was also used for the transfection not digested with Csp45I as a circular form. The culture medium was removed from the confluent 293 cells in a 6-cm dish, and all the mixture of the plasmid and the reagent were added to the culture dish and 293 cells were cultured at 37° C. for one hour. Thereafter, 3 ml of DMEM medium supplemented with 5% FCS (hereinafter it is called simply medium) was added to the dish and cells were cultured furthermore. After 16 hours, the medium was replaced to the fresh medium and cells were harvested from the dish and suspended in 11 ml of the medium. On the other hand, untransfected 293 cells in a 6-cm dish were harvested, and suspended in 10 ml of the medium. An aliquot of 1.1 ml was taken from 11 ml of the transfected cells, mixed with 9 ml of untransfected cells, and these cells were plated to a 96-well plate coated with collagen in a ratio of 100 µl/well (10-fold dilution plate). The remaining transfected cells were plated in another 96-well plate in a ratio of 100 µl/well (1-fold dilution plate) in the same manner. Each plate was cultured at 37° C. in the atmosphere of 5% CO$_2$. A 50 µl of fresh medium was added after 5 days and 10 days.

3 days after transfection, the appearance of the cytopathicity was observed everyday; at the same time, the expression of RedE protein emitting the red fluorescence was observed by the fluorescent microscope (excitation wavelength: 558 nm/radiation wavelength: 583 nm) in the case of cells transfected with cosmid vectors harboring the RedE expression units (pAxCARedE, pAxCARedEith, pAxCARedEit). As a result, the expression of RedE protein was confirmed in cells transfected with pAxCARedEit. However, the time of expression differs depending upon clones. Some clones expressed the RedE protein relatively earlier time, that is, 5 to 6 days after the transfection and other clones started to express relatively late time, that is, 8 to 10 days after the transfection. Then any 5 clones were picked up from the former group and 4 clones from the latter group. After cells were completely degenerated, the cell suspensions were collected in a 1.5 ml-volume micro-centrifuge tube, and sonicated with a sealed type sonicator (200 W, 30 seconds×3 times) and thereafter centrifuged by a micro-centrifuge (at 5,000 rpm for 5 minutes). The supernatant was recovered as a viral solution.

On the other hand, 293 cells were cultured confluently in a 24-well plate coated with collagen. From the plate, the medium was removed except for about 100 µl, then, 10 µl of the viral solution recovered above was added to the plate and incubated at 37° C. for one hour. After the cells were infected with the viruses, 0.4 ml of medium was added and cultured at 37° C. Three to four days after, the cells were completely degenerated, cells were collected. After the cells were suspended well in 400 µl of TNE buffer (50 mM Tris.HCl (pH8.0)/100 mM NaCl/10 mM EDTA) containing 100 µg/ml proteinase K, added 4 µl of 10% SDS solution, and then heated at 50° C. for 2 hours. Subsequently, the reaction mixture was extracted with phenol/chloroform twice and with chloroform twice, and then precipitated with ethanol. The DNA precipitated was dissolved in 50 µl of TE buffer containing 20 µg/ml RNase A. Finally, the recovered DNA was digested with restriction enzyme SmaI or ClaI and then subjected to agarose gel electrophoresis to confirm whether a desired adenovirus was generated or not (FIG. 7).

The lower part of FIG. 7 schematically shows the sizes of bands generated with restriction enzyme digestion. If the desired adenovirus is generated, about 0.45 kb band containing the left terminal of the viral genome, and about 1.7 kb, 0.74 kb and 0.57 kb bands derived from expression units were generated by ClaI digestion. On the other hand, 0.58 kb band containing the right terminal of the viral genome was generated by SmaI digestion. As shown in the photographs of agarose gel electrophoresis, not only 5 clones early expressing RedE protein but also 4 clones lately expressing it, all give bands as is predicted in ClaI digestion and SmaI digestion. As a result, it was demonstrated that a desired recombinant adenovirus can be obtained with substantially a 100% frequency by use of the cosmid vector having both terminals in complete form according to the present invention.

Next, the number of recombinant adenoviral clones obtained by use of cosmid vectors pAxCARedE (both terminals deletion type), pAxCARedEith (the left terminal complete type), and pAxCARedEit (both terminals complete type) was compared. The experiment was repeated twice. In the first experiment, cosmid DNA fragments all digested with Csp45I were used in transfection. As a result, no recombinant adenoviruses were obtained in cosmid pAxCARedE (both terminals deletion type) and cosmid pAxCARedEith (the left terminal complete type). However, in cosmid pAxCARedEit (both terminals complete type), a sufficiently large number of recombinant adenoviruses were obtained (340 clones per 10 µg cosmid DNA) (Table 1). In the second experiment, a circular-form cosmid, pAxCARedEit (both terminals complete type) not digested with Csp45I was included for transfection. However, no recombinant adenoviruses were obtained if the cosmid vector was not digested with Csp45I. It is therefore demonstrated that it is necessary to transfect after a cosmid of both terminals complete type is digested with a restriction enzyme, thereby linearizing the adenoviral genome portion (Table 1).

Furthermore a cosmid vector having another gene (GFP) was examined. More specifically, 293 cells were transfected with 10 µg of cosmid pAxCAGFP (both terminals deletion type) or pAxCAGFPit (both terminals complete type), by use of a transfection reagent, TransFast (registered trade mark) or CellPhect transfection kit (the company, Amersham-Pharmacia). In the same manner as in the case of cosmid pAxCARedEit, transfected cells were diluted and seeded in a 96-well plate and the number of recombinant adenoviral clones generated was counted. The results are shown in Table 1. No adenoviruses were obtained when cells were transfected with a cosmid of both terminals deletion type. Only in the case where cells were transfected with a cosmid of both terminals complete type, a sufficiently large number of recombinant adenoviruses were obtained (50 to 80 clones/10 µg cosmid DNA). Of them, 10 clones were picked up and the structure of the adenoviral genome was analyzed by restriction enzyme digestion of genomic DNA in the same manner as in the case of pAxCARedEit. Although data is not shown, it was confirmed that all clones are desired recombinant adenoviruses.

From the results mentioned above, it was demonstrated that a recombinant adenoviral vector having a desired gene integrated therein can be efficiently generated by use of a cosmid vector of both terminals complete type according to the present invention.

TABLE 1

Comparison of various type of cosmid vectors in generation efficiency of recombinant adenovirus by use of "cloned-genome introducing method"

| cDNA | Cosmid | Transfection reagent | Number of viral clones (per 10 µg DNA) | |
|---|---|---|---|---|
| | | | Experiment 1 | Experiment 2 |
| RedE | Both terminals deletion type (pAxCARedE) | TransFast ™ | 0 | 0 |
| | The left terminal complete type (pAxCARedEith) | TransFast ™ | 0 | 1 |
| | Both terminals complete type (pAxCARedEit) | TransFast ™ | 340 | 190 |
| | Both terminals complete type (uncut) | TransFast ™ | ND | 0 |
| GFP | Both terminals deletion type (pAxCAGFP) | TransFast ™ CellPhect | 0 0 | |
| | Both terminals complete type (pAxCARGFPit) | TransFast ™ CellPhect | 50 80 | |

RedE: Red fluorescent protein derived from coral
GFP: Green fluorescent protein derived from jellyfish
ND: Not determined Example 5

Generation of Recombinant Adenoviral Vector by the COS-TPC Method

The following experiments were performed to confirm that the cosmid vector of both terminals complete type can be applied to homologous recombination method (COS-TPC method) between adenoviral genome DNA with a terminal protein (DNA-TPC) and a cosmid vector.

As the DNA-TPC, DNA-TPC was used containing in a commercially available recombinant adenoviral construction kit, namely, Adenovirus Expression Vector Kit (the company, Takara Bio, #6150). 293 cells were transfected with 8 µg of cosmid DNA of pAxCARedE (both terminals deletion type) or cosmid DNA of pAxCARedEit (both terminals complete type) and 5 µl of DNA-TPC containing in the kit which is digested with a restriction enzyme previously, in the manner shown in Example 4 using a transfection reagent, TransFast (registered trade mark) or CellPhect transfection kit. The following day, the cells were seeded in a 96-well plate. Based on the number of wells having degenerated cells, the number of adenoviruses generated was calculated. The results are shown in Table 2. Also the number of recombinant adenoviruses when the cosmid of both terminals complete type was used is the same when a conventional cosmid of both terminals deletion type. From this, it was confirmed that the cosmid of both terminals complete type can be used in generating a recombinant adenovirus by the COS-TPC method.

Although the COS-TPC was used, there was no difference in the number of recombinant adenoviruses generated compared to the case where cells were transfected with the cosmid alone. In previous data by the present inventors in the COS-TPC method, about 1000 clones of a recombinant adenovirus are generated per 10 µg cosmid DNA (Miyake S. et. Al., Proc. Natl. Acad. Sci. USA, Vol. 93, 1320-1324. (1996)). From this, the reason why there is no difference between transfection by the COS-TPC method and transfection by a cosmid alone is not clear but considered that the generation efficiency of a recombinant virus by the COS-TPC method at this time was low.

TABLE 2

Generation efficiency of a recombinant virus by COS-TPC method

| Cosmid | Transfection reagent | The number of adenovirus clones (per 10 µg DNA) |
|---|---|---|
| Both terminals deletion type (pAxCARedE) | TransFast ™ CellPhect | 220 250 |
| Both terminals complete type (pAxCARedEit) | TransFast ™ CellPhect | 190 330 |

Example 6

Construction of Cosmid Vector having a Multiple Kinds of Restriction Enzyme Recognition Sites Added to both Terminals of the Adenoviral Genome <1> After a plasmid pxCAEGFP used in Example 2 (FIG. 8 (L)) having a GFP gene inserted downstream of the CAG promoter was digested with AseI and ClaI, and blunt-ended with Klenow to prepare a DNA fragment of 773 bp containing the GFP gene. On the other hand, a plasmid pCAwG (FIG. 8(M)) was identical with pCAGw (JP-A-8-84589, page 10). An EcoRI site, which is a cloning site of plasmid pCAGGS (Niwa et. al., Gene, Vol. 108, 193-200(1991)) containing the CAG promoter, was replaced for SwaI site in pCAGw. The DNA fragment of 773 bp was inserted into the SwaI site of plasmid pCAwG to obtain plasmid pCAGFPdc (5.6 kb, FIG. 8(N)), in which the GFP gene was introduced in the same direction as the promoter.

<2> The following manipulation were performed to construct a cosmid vector having a GFP expression unit inserted therein and deleting the SwaI site and the ClaI site from the cosmid vector pAxcwit (FIG. 5(K) and FIG. 8(K)) constructed in Example 1. After the plasmid pCAGFPdc was digested with HindIII and blunt-ended with Klenow enzyme, and a SalI linker (5'-GGTCGACC) was ligated, and then digested with AccI, which recognizes the same nucleotide sequence as the SalI site to obtain a DNA fragment of about 3.0 kb containing—a GFP expression unit. The fragment digested with AccI generates the same protruding end as that of a ClaI digestion fragment. Therefore, both fragments could be ligated. Then, the plasmid pAxcwit was digested with ClaI and the above DNA fragment of about 3.0 kb was ligated to obtain a cosmid vector pAxCAGFPitdcp (45.6 kb. FIG. 8(O)) having a GFP expression unit inserted in the left side orientation (reverse direction of the E1 gene transcription direction).

<3> There are three Csp45I sites present in a cosmid vector pAxCAGFPitdcp. To delete the Csp45I sites near the COS region, the cosmid vector pAxCAGFPitdcp is partially digested with Csp45I, and blunt-ended with Klenow enzyme, and self ligated to obtain a cosmid vector pAxCAGFPitdcp2b (45.6 kb, FIG. 8(P)) in which the Csp45I near the COS region alone was deleted.

<4> To construct a cosmid vector further having a SwaI site-ClaI site-PacI site outside the Csp45I sites of both terminals of the adenoviral genome, the following manipulation were performed.

(1) The following two oligo DNA fragments were synthesized which contained a SwaI site, ClaI site, and PacI site in this order and designed so as to protrude 2 nucleotides from the 5' end of both terminals when annealed, and to be able to ligate with a fragment digested with Csp45I. The 5' ends of these oligo DNAs were phosphorylated and then annealed to prepare a synthetic polylinker (FIG. 9).

(Sequence ID No. 3)
5'-CGATTTAAATATCGATTTAATTAATT-3'

(Sequence ID No. 4)
5'-CGAATTAATTAAATCGATATTTAAAT-3'

Both terminals of this polylinker is capable of ligating to the Csp45I digested fragment. However, the Csp45I site can be regenerated only when the terminal near the PacI site is ligated with the Csp45I digested fragment.

(2) The cosmid vector pAxCAGFPitdcp2b was digested with Csp45I and cleaved to a DNA fragment of about 34 kb containing the adenoviral genome and a DNA fragment of about 11.4 kb not containing the adenoviral genome. The mixture of both DNA fragments was added with an excess amount (150 folds by molar ratio) of synthetic polylinker prepared in the step (1) and ligated. To remove a multi-copy of polylinkers ligated to both terminals of both DNA fragments, the DNA after ligation was digested with ClaI and subjected to the electrophoresis, and then short DNA fragments not ligated to both DNA fragments were removed. By this operation, the DNA fragment of about 34 kb or 11.4 kb in which both terminals were ClaI digested fragments and a SwaI site or a PacI site were present inside the terminals, was obtained. Finally, both DNA fragments were ligated to obtain a cosmid vector psbAxGbs (45.7 kb, FIG. 9 (Q)) having an adenoviral genome portion, an ampicillin resistant gene, an *Escherichia coli* replication origin, and a COS region arranged in the same position as in the cosmid vector pAxCAGFPitdcp2b and having restriction sites of a SwaI site-a ClaI site-a PacI site-a Csp45I site-the adenoviral genome-a Csp45I site-a PacI site-a ClaI site-a SwaI site arranged in this order.

Example 7

Comparison of Cosmid Vectors Digested at Different Restriction Enzyme Recognition Sites in the Generation Efficiency of an Adenoviral Vector The cosmid vector psbAxGbs constructed in Example 6 was digested with Csp45I, ClaI or SwaI. After 293 cells were transfected with 10 μg of each DNA in accordance with the method shown in Example 4 (using TransFast), the cells were seeded in a 96-well plate. After 17 days, the number of wells where cells were degenerated due to the generation of recombinant adenoviruses and rate of cells expressing GFP reached 75% or more was counted and regarded as the number of viral clones generated.

The experiment was repeated twice. In the first experiment, cells were transfected with cosmids digested with Csp45I or SwaI and in the second experiment, cells were transfected with cosmids digested with Csp45I, ClaI or SwaI.

The results are shown in Table 3. Both experiments show that the number of viruses generated in the case of using cosmids digested with SwaI is clearly low compared to the case of using cosmids digested with Csp45I. The number of viruses generated in the case of using cosmids digested with ClaI was intermediate between both cases (Experiment 2).

TABLE 3

Comparison of cosmid vectors digested at different restriction sites in the generation efficiency of an adenoviral vector

| Restriction enzyme | Average number of nucleotides from the terminal(s) of adenoviral genome | The number of viral clones (per 10 μg DNA) | |
|---|---|---|---|
| | | Experiment 1 | Experiment 2 |
| Csp45I | 3 bp | 74(100%) | 65(100%) |
| ClaI | 14 bp | ND | 44(68%) |
| SwaI | 21 bp | 29(39%) | 36(55%) |

ND: Not done

From the results, even if a cosmid is cleaved at the cleavage site (SwaI) which is positioned 21 nucleotides outside the terminals of the adenoviral genome, which is more distant from the cleavage site (Csp45I) which is positioned at 3 nucleotides outside thereof, the generation efficiency of virus slightly reduced but the reduced levels was within about ⅓ in the case of Csp45I. Therefore, it is clear that a cosmid vector having a multiple kinds of cleavage sites of virus genome outside the terminal(s) of the adenoviral genome is useful. Furthermore, the results suggest the possibility that if the cleavage site of the adenovirus genome is closer to the terminal, the efficiency of generating recombinant adenoviruses is higher.

INDUSTRIAL APPLICABILITY

According to the present invention, there is provided a novel cosmid vector effectively used in generating a recombinant adenoviral vector. Since the novel cosmid vector of the present invention is simple, practical and applicable to both the COS-TPC method and the "cloned-full-length genome introducing method", it is effectively used in generating a recombinant adenoviral vector.

SEQUENCE LISTING FREE TEXT

The nucleotide sequence described under Sequence ID No. 1 is a synthetic oligonucleotide.
The nucleotide sequence described under Sequence ID No. 2 is a synthetic oligonucleotide.
The nucleotide sequence described under Sequence ID No. 3 is a synthetic oligonucleotide.
The nucleotide sequence described under Sequence ID No. 4 is a synthetic oligonucleotide.

The invention claimed is:

1. A cosmid vector comprising:
   (1) an adenoviral genome having a left-inverted terminal repeat and a right-inverted terminal repeat, each of said repeats having a complete nucleotide sequence,
   (2) a deletion in an adenovirus E1 gene region, wherein the E1 gene deletion site comprises a restriction enzyme recognition sequence at the E1 gene deletion site,
   (3) a first pair of identical restriction enzyme recognition sequences, wherein said first pair of sequences are not naturally present in the adenoviral genome, one of said sequences in the first pair is located on the left side of the left-inverted terminal repeat and the other of said sequences in the first pair is located on the right side of the right-inverted terminal repeat;
   (4) a drug resistant gene, a replication origin, a spacer sequence and a COS region in this order from outside of the left-inverted terminal repeat sequence toward the right inverted terminal repeat sequence,
   (5) a second pair of identical restriction enzyme recognition sequences, wherein one of said sequences in the second pair is located at the E1 gene deletion site and at a right side of the restriction enzyme recognition sequence in (2), and the other of said sequences in the second pair is present inside the spacer sequence.

2. The cosmid vector according to claim 1, comprising the sequence TTCGAA, which can be recognized by at least Csp45I, BspT104I or BstBI, as a restriction enzyme recognition sequence present on both sides of the adenoviral genome.

3. The cosmid vector according to claim 1, wherein the restriction enzyme recognition sequence at the E1 gene deletion site is a SwaI recognition sequence.

4. The cosmid vector according to claim 1, wherein the cosmid vector further comprising a CAG promoter or an EF-1α promoter at the E1 gene deletion site.

5. A composition for generating a recombinant adenoviral vector comprising the cosmid vector according to claim 1 as a component, in an admixture with a suitable diluent.

6. The cosmic vector according to claim 1, wherein the second pair of restriction enzyme recognition sequences are SalI recognition sequence or NruI recognition sequence.

7. The cosmid vector according to claim 1, comprising at least two pairs of identical restriction enzyme recognition sequences which are not present in the adenoviral genome and exist on both sides of the adenoviral genome.

8. The cosmid vector according to claim 7, wherein the two pairs of identical restriction enzyme recognition sequences are selected from the group consisting of (a) TTCGAA recognized by a restriction enzyme Csp45I, BspT104I, or BstBI, (b) TTAATTAA recognized by a restriction enzyme PacI, and (c) ATCGAT recognized by a restriction enzyme ClaI or BspDI.

9. The cosmid vector according to claim 8, wherein the two pairs of identical restriction enzyme recognition sequences are (a) TTCGAA recognized by a restriction enzyme Csp45I, BspT104I, or BstBI, or (b) TTAATTAA recognized by a restriction enzyme PacI.

10. The cosmid vector according to claim 8, wherein the two pairs of identical restriction enzyme recognition sequences are (a) TTCGAA recognized by a restriction enzyme Csp45I, BspT104I, or BstBI, or (c) ATCGAT recognized by a restriction enzyme ClaI or BspDI.

11. The cosmid vector according to claim 1, wherein the vector does not comprise additional restriction enzyme recognition sequences which are identical to the second pair of identical restriction enzyme recognition sequences, in a region containing one of the sequences in the second pair located at the E1 gene deletion site, the drug resistance gene, the replication origin and the other of the sequences in the second pair located inside the spacer sequence.

* * * * *

SEQUENCE LISTING

<160> NUMBER OF SEQ ID NOS: 4

<210> SEQ ID NO 1
<211> LENGTH: 44

```
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 1
gatccgcatg catcatcaat aatataccttt attttggatt gaag                    44

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 2
cttcaatcca aaataaggta tattattcat gatgcatgcg                          40

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 3
cgatttaaat atcgatttaa ttaatt                                         26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 4
cgaattaatt aaatcgatat ttaaat                                         26
```